United States Patent

Brewster et al.

[11] Patent Number: 5,981,531
[45] Date of Patent: Nov. 9, 1999

[54] ACID DERIVATIVES

[75] Inventors: Andrew George Brewster; Peter William Rodney Caulkett; Alan Wellington Faull, all of Macclesfield; Robert James Pearce, Wilmslow; Richard Eden Shute, Macclesfield, all of United Kingdom

[73] Assignee: Zeneca Limited, London, United Kingdom

[21] Appl. No.: 09/086,408

[22] Filed: May 29, 1998

Related U.S. Application Data

[62] Division of application No. 08/767,443, Dec. 16, 1996, Pat. No. 5,760,057, which is a division of application No. 08/266,375, Jun. 27, 1994, Pat. No. 5,612,373.

[30] Foreign Application Priority Data

Jun. 28, 1993 [GB] United Kingdom .................. 9313285

[51] Int. Cl.$^6$ ...................... C07D 241/04; C07D 401/12; C07D 403/12; A61K 31/495
[52] U.S. Cl. .......................... 514/255; 544/390; 544/400; 544/405
[58] Field of Search ................................... 544/390, 400, 544/405; 514/255

[56] References Cited

U.S. PATENT DOCUMENTS

| | | | |
|---|---|---|---|
| 5,039,805 | 8/1991 | Alig et al. | 546/224 |
| 5,084,466 | 1/1992 | Alig et al. | 514/353 |
| 5,227,490 | 7/1993 | Hartman et al. | 514/317 |
| 5,254,573 | 10/1993 | Bovy et al. | 514/357 |
| 5,264,420 | 11/1993 | Duggan et al. | 514/317 |
| 5,276,049 | 1/1994 | Himmelsbach et al. | 514/392 |
| 5,281,585 | 1/1994 | Duggan et al. | 514/79 |
| 5,563,143 | 10/1996 | Cohan et al. | 514/256 |

FOREIGN PATENT DOCUMENTS

| | | |
|---|---|---|
| 74101 | 10/1991 | Australia . |
| 10403 | 7/1992 | Australia . |
| 20569 | 1/1993 | Australia . |
| 21119 | 2/1993 | Australia . |
| 20892 | 3/1993 | Australia . |
| 27062 | 4/1993 | Australia . |
| 41201 | 12/1993 | Australia . |
| 2008116 | 9/1990 | Canada . |
| 2037153 | 9/1991 | Canada . |
| 2060661 | 9/1992 | Canada . |
| 2093770 | 10/1993 | Canada . |
| 2094773 | 10/1993 | Canada . |
| 0007648 | 6/1980 | European Pat. Off. . |
| 0116729 | 8/1984 | European Pat. Off. . |
| 0136745 | 10/1985 | European Pat. Off. . |
| 0475506 | 3/1992 | European Pat. Off. . |
| 0478328 | 4/1992 | European Pat. Off. . |
| 0478362 | 4/1992 | European Pat. Off. . |
| 0478363 | 4/1992 | European Pat. Off. . |
| 0479481 | 4/1992 | European Pat. Off. . |
| 0512829 | 11/1992 | European Pat. Off. . |
| 0512831 | 11/1992 | European Pat. Off. . |
| 0513675 | 11/1992 | European Pat. Off. . |
| 0529858 | 3/1993 | European Pat. Off. . |
| 0539343 | 4/1993 | European Pat. Off. . |
| 07867 | 4/1993 | European Pat. Off. . |
| 0540334 | 5/1993 | European Pat. Off. . |
| 0560730 | 9/1993 | European Pat. Off. . |
| 05562 | 5/1991 | WIPO . |
| 13552 | 8/1992 | WIPO . |
| 17196 | 10/1992 | WIPO . |
| 18117 | 10/1992 | WIPO . |
| 01874 | 4/1993 | WIPO . |
| 08181 | 4/1993 | WIPO . |
| 10091 | 5/1993 | WIPO . |
| 12074 | 6/1993 | WIPO . |
| 14077 | 7/1993 | WIPO . |
| 16038 | 8/1993 | WIPO . |
| 19046 | 9/1993 | WIPO . |
| 22303 | 11/1993 | WIPO . |
| 01396 | 1/1994 | WIPO . |

OTHER PUBLICATIONS

Alig et al., "Low Molecular Weight, non–peptide Fibrinogen Receptor Antagonists," J. Med. Chem., 1992, 35, 4393–4407.

Hartman et al., "Non–peptide Fibrinogen Receptor Antagonists 1. Discovery and Design of Exosite Inhibitors," J. Med. Chem., 1992, 35, 4640–4642.

*Primary Examiner*—Alan L. Rotman
*Attorney, Agent, or Firm*—Pillsbury Madison & Sutro, LLP

[57] ABSTRACT

The invention concerns acid derivatives of formula I $$R^1—CON(R^2)—N(R^3)CO—X^1—Q—X^2—G$$

and pharmaceutically acceptable metabolically labile esters or amides thereof, and pharmaceutically acceptable salts thereof, in which $R^1$, $R^2$, $R^3$, $X^1$, Q, $X^2$ and G have the meanings given in the specification. The invention also concerns processes for the preparation of the acid derivatives of formula I, pharmaceutical compositions containing them and their use as inhibitors of the binding of fibrinogen to glycoprotein IIb/IIIa.

8 Claims, No Drawings

ACID DERIVATIVES

This is a division of application Ser. No. 08/767,443, filed Dec. 16, 1996, U.S. Pat. No. 5,760,057, which is a divisional of application Ser. No. 08/266,375 filed Jun. 27, 1994, U.S. Pat. No. 5,612,373.

The present invention relates to a group of acid derivatives which inhibit cell adhesion (for example, platelet aggregation), to processes for their preparation and to pharmaceutical compositions containing them.

A variety of diseases involve cell adhesion during their development. For example, platelet aggregation is involved in the formation of blood thrombi, which can lead to diseases such as thrombosis, (for example stroke and thrombotic events accompanying unstable angina and transient ischaemic attack), myocardial infarction, atherosclerosis, thromboembolism and reocclusion during and after thrombolytic therapy.

It is widely believed that the platelet membrane glycoprotein IIb-IIIa (GPIIb-IIIa) mediates platelet aggregation. Adhesion molecules such as fibrinogen and von Willebrand Factor are believed to bind to GPIIb-IIIa sites on adjacent platelets and thereby cause them to aggregate. Other adhesion molecules which are known to bind to the GPIIb-IIIa are fibronectin, vitronectin and thrombospondin.

Compounds which inhibit platelet aggregation and the binding of adhesion molecules to GPIIb-IIIa are known, for example from U.S. Pat. Nos. 5,039,805 and 5,084,446, Canadian patent applications numbers 2,008,161, 2,037,153 and 2,061,661, and Alig et al., J. Med. Chem., 1992, 35, 4393–4407. Commonly the structures of these compounds are based upon the binding regions of the adhesion molecules, which are peptides. For example, a portion of fibrinogen which is believed to bind to GPIIb-IIIa is the amino acid sequence RGD (arginyl glycyl aspartate).

The ability to inhibit platelet aggregation and to inhibit the binding of fibrinogen to GPIIb-IIIa has now been found to be possessed by certain acid derivatives containing an acylcarbazolyl group.

According to one aspect, therefore, the present invention provides a compound of the general formula I (formula set out at the end of the description together with the other formulae referred to herein by Roman numerals)
wherein $R^1$ represents a group of formula II or III in which
A is attached meta or para to the position where the group $CONR^2NR^3CO$ is attached and is selected from aminomethyl, guanidino and $R^aN=C(NH_2)$— where $R^a$ is hydrogen or phenyl which is unsubstituted or substituted by 1 or 2 of halogeno, (1–4C)alkyl, (1–4C)alkoxy, cyano and nitro,
E is CH or N,
$Z^1$ is hydrogen, halogeno, (1–4C)alkyl, (1–4C)alkoxy, cyano or nitro,
T is N or CH, and
$X^3$ is a bond, (1–4C)alkylene or, when T is CH, oxy(1–3C)alkylene;
2 3 $R^2$ and $R^3$, which may be the same or different, represent hydrogen, (1–4C)alkyl or ar(1–4C)alkyl;
$X^1$ is a bond or (1–4C)alkylene;
Q is a group of formula IV or V in which $Z^2$ is hydrogen, halogeno, (1–4C)alkyl, (1–4C)alkoxy, cyano or nitro, and $Z^3$ is a group of formula $X^2$—$G^a$ in which $X^2$ can have any of the values given hereinafter for $X^2$ and $G^a$ can have any of the values given hereinafter for G, or $G^a$ has any of the values given hereinbefore for $Z^2$;
$X^2$ is a bond, (1–4C)alkylene, oxy(1–3C)alkylene or a group of formula $CH_2CH(NHXR^4)$ in which X is $SO_2$, CO or $CO_2$ and $R^4$ is (1–6C)alkyl, (6–12C)aryl or (6–12C)aryl (1–4C)alkyl in which the aryl group may optionally be substituted by (1–4C)alkyl; and
G is a carboxy group or a pharmaceutically acceptable metabolically labile ester or amide thereof; and
pharmaceutically acceptable salts thereof.

It will be appreciated that depending on the nature of the substituents, in containing one or more chiral centres, the formula I compounds may exist in and be isolated in one or more different enantiomeric or racemic forms (or a mixture thereof). It is to be understood that the invention includes any of such forms which possesses the property of inhibiting platelet aggregation and inhibiting the binding of fibrinogen to GpIIb-IIIa, it being well known how to prepare individual enantiomeric forms, for example, by synthesis from appropriate chiral starting materials or by resolution of a racemic form. Similarly, the biological properties of a particular form may be readily evaluated, for example by use of one or more of the standard in vitro or ex vivo screening tests detailed hereinbelow.

It will also be appreciated that compounds of formula I wherein $R^1$ represents a group of formula II and A represents the group $R^aN=C(NH_2)$— may exist in tautomeric forms, and that the invention includes the compounds in any of their tautomeric forms.

A is preferably a group of formula $R^aN=C(NH_2)$—. It is preferably attached para to the position where the group $CONR^2NR^3CO$ is attached.

Examples of values for $R^a$ include hydrogen and phenyl. Examples of substituents on $R^a$ when it is phenyl include fluoro, chloro, bromo, methyl, ethyl, methoxy, ethoxy, cyano and nitro.

When $R^1$ represents a group of formula II bearing the substituent $Z^1$, $Z^1$ may represent, for example, hydrogen, fluoro, chloro, bromo, methyl, ethyl, methoxy, ethoxy, cyano or nitro.

When $R^1$ represents a group of formula III, examples of values for $X^3$ include a bond, methylene, ethylene, trimethylene and, when T is CH, oxymethylene.

Examples of values for $R^1$ include 3-aminomethylphenyl, 4-aminomethylphenyl, 4-amidinophenyl, 4-($N^2$-phenyl)amidinophenyl, piperidin-4-yl, piperidin-4-ylmethyl, 2-piperidin-4-ylethyl, 6-amidinopyrid-3-yl, 5-amidinopyrid-2-yl, piperidin-4-yloxymethyl and piperazin-1-yl.

A (1–4C)alkyl group represented by $R^2$ or $R^3$ may be, for example, methyl or ethyl. An ar(1–4C)alkyl may be, for example, benzyl. Preferably one of $R^2$ and $R^3$ is hydrogen and the other is hydrogen, methyl or benzyl. More preferably each of $R^2$ and $R^3$ represents hydrogen.

Examples of values for $X^1$ when it represents (1–4C) alkylene are methylene and ethylene. Preferably $X^1$ represents a bond.

In the group Q, when it is a group of formula IV, examples of values for $Z^2$ include hydrogen, fluoro, chloro, bromo, methyl, ethyl, methoxy, ethoxy, cyano and nitro. Hydrogen is a preferred value for $Z^2$.

In the group Q, when it is a group of formula IV or V, and $Z^3$ is a group of formula $X^2$—$G^a$, examples of values for $X^2$ include a bond, methylene, ethylene, oxymethylene and groups of formula $CH_2CH(NHXR^4)$ in which X is $SO_2$, CO or $CO_2$ and $R^4$ is methyl, ethyl, propyl, butyl, pentyl, phenyl, tolyl or benzyl, and examples of values for $G^a$ include carboxy (or a pharmaceutically acceptable metabolically labile ester or amide thereof), hydrogen, fluoro, chloro, bromo, methyl, ethyl, methoxy, ethoxy, cyano and nitro. Preferably $Z^3$ is hydrogen or a group of formula $X^2$—$G^a$ in which $X^2$ is oxymethylene and $G^a$ is carboxy.

Examples of values for $X^2$ include a bond, methylene, ethylene, oxymethylene, oxyethylene and groups of formula $CH_2CH(NHXR^4)$ in which X is $SO_2$, CO or $CO_2$ and $R^4$ is methyl, ethyl, propyl, butyl, pentyl, phenyl, tolyl or benzyl. Preferably $X^2$ is oxymethylene or a group of formula $CH_2CH(NHSO_2(CH_2)CH_3)$.

Examples of ester derivatives of a carboxy group represented by G include esters formed with alcohols such as (1–6C)alkanols, for example methanol, ethanol, propanol and t-butanol; indanol; benzyl alcohol; adamantol; (1–6C) alkanoyloxy(1–4C)alkanols such as pivaloyloxymethanol; glycolamides; (5-methyl-2-oxo-1,3-dioxol-4-yl)methyl alcohol; and (1–4C)alkoxycarbonyl(1–4C)alkanols.

Examples of amide derivatives of a carboxy group represented by G include amides derived from ammonia and amines such as (1–4C)alkylamines, for example methylamine; di(1–4C)alkylamines, for example dimethylamine; (1–4C)alkoxy(1–4C)alkylamines such as methoxyethylamine; and amino acids such as glycine or an ester thereof.

Preferably G represents a carboxy group or a (1–4C) alkoxycarbonyl group such as methoxycarbonyl, ethoxycarbonyl or t-butoxycarbonyl.

Particular pharmaceutically acceptable salts include, for example, salts with acids affording physiologically acceptable anions, such as salts with mineral acids, for example a hydrogen halide (such as hydrogen chloride and hydrogen bromide), sulphuric acid or phosphoric acid, and salts with organic acids, for example acetic acid and trifluoroacetic acid. Other pharmaceutically acceptable salts include, for example salts with inorganic bases such as alkali metal and alkaline earth metal salts (for example sodium salts), ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethyl-ammonium hydroxide.

Particular compounds of the invention include, for example, acid derivatives of formula I, or pharmaceutically acceptable salts thereof, in which, unless otherwise stated, each of the variable groups $R^1$, $R^2$, $R^3$, Q, $X^2$ and G have any of the meanings defined hereinbefore or in this section concerning particular compounds of the invention:

(a) $R^1$ represents a group of formula II in which A is attached para to the position where the group $CONR^2NR^3CO$ is attached and is selected from aminomethyl, guanidino and $R^aN=C(NH_2)$— where R is hydrogen or phenyl, E is CH or N, and $Z^1$ is hydrogen, fluoro, chloro, methyl, methoxy or cyano;

(b) $R^1$ represents a group of formula III in which T is CH or N, and $X^3$ is a bond, methylene, ethylene, trimethylene or, when T is CH, oxymethylene;

(c) $R^2$ and $R^3$ which may be the same or different, represent hydrogen, methyl, ethyl or benzyl;

(d) $X^1$ is a bond or methylene;

(e) Q is a group of formula IV in which $Z^2$ is hydrogen, fluoro, chloro, methyl, methoxy or cyano, and $Z^3$ is hydrogen or a group of formula $X^2$—$G^a$ in which $X^2$ is methylene, ethylene or oxymethylene and $G^a$ is a carboxy group or a pharmaceutically acceptable metabolically labile ester thereof;

(f) Q is a group of formula V in which $Z^3$ is hydrogen or a group of formula $X^2$—$G^a$ in which $X^2$ is methylene, ethylene or oxymethylene and $G^a$ is a carboxy group or a pharmaceutically acceptable metabolically labile ester thereof;

(g) $X^2$ is methylene, ethylene or oxymethylene; and (h) G is a carboxy group or a pharmaceutically acceptable metabolically labile ester thereof.

A preferred compound of the invention is an acid derivative of formula I wherein $R^1$ represents a group of formula II in which A is attached para to the position where the group $CONR^2NR^3CO$ is attached and is selected from aminomethyl and a group of formula $R^aN=C(NH_2)$— where $R^a$ is hydrogen or phenyl, E is CH and $Z^1$ is hydrogen, fluoro, chloro, methyl or methoxy;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2$—$G^a$ in which $X^2$ is oxymethylene and $G^a$ is carboxy, methoxycarbonyl or ethoxycarbonyl;

$X^2$ is oxymethylene; and

G is carboxy, methoxycarbonyl, ethoxycarbonyl, propoxycarbonyl or t-butoxycarbonyl;

or a pharmaceutically acceptable salt thereof.

A further preferred compound of the invention is an acid derivative of formula I wherein $R^1$ represents a group of formula III in which T is CH or N, and $X^3$ is a bond, methylene, ethylene or, when T is CH, oxymethylene;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2$—$G^a$ in which $X^2$ is oxymethylene and $G^a$ is carboxy, methoxycarbonyl or ethoxycarbonyl;

$X^2$ is oxymethylene; and

G is carboxy, methoxycarbonyl, ethoxycarbonyl, propoxycarbonyl or t-butoxycarbonyl;

or a pharmaceutically acceptable salt thereof.

A further preferred compound of the invention is an acid derivative of formula I wherein $R^1$ represents a group of formula II in which A is attached para to the position where the group $CONR^2NR^3CO$ is attached and is a group of formula $R^aN=C(NH_2)$— where $R^a$ is hydrogen or phenyl, E is CH and $Z^1$ is hydrogen;

$R^2$ is hydrogen;

$R^3$ is hydrogen or methyl;

$X^1$ is a bond;

Q is a group of formula IV in which $Z^2$ is hydrogen and $Z^3$ is hydrogen or a group of formula $X^2$—$G^a$ in which $X^2$ is oxymethylene and $G^a$ is carboxy;

X is oxymethylene; and

G is carboxy, methoxycarbonyl, ethoxycarbonyl or t-butoxycarbonyl; or a pharmaceutically acceptable salt thereof.

A further preferred compound of the invention is an acid derivative of formula I wherein $R^1$ represents a group of formula III in which T is CH and $X^3$ is ethylene;

$R^2$ is hydrogen;

$R^3$ is hydrogen or methyl;

$X^1$ is a bond;

Q is a group of formula IV in which $Z^2$ is hydrogen and $Z^3$ is hydrogen or a group of formula $X^2$ —$G^a$ in which X is oxymethylene and $G^a$ is carboxy;

$X^2$ is oxymethylene; and

G is carboxy, methoxycarbonyl, ethoxycarbonyl or t-butoxycarbonyl; or a pharmaceutically acceptable salt thereof.

Specific especially preferred compounds of the invention include acid derivatives of formula I selected from:
4-[3-(3-piperidin-4-ylpropanoyl)carbazoyl]-2-(carboxymethoxy)-phenoxyacetic acid,
4-[3-(2-piperidin-4-yloxyacetyl)carbazoyl]-2-(carboxymethoxy)-phenoxyacetic acid,
4-[3-(4-aminomethylbenzoyl)carbazoyl]-2-(carboxymethoxy)phenoxyacetic acid,
4-[3-(4-amidinobenzoyl)carbazoyl]phenoxyacetic acid,
methyl 4-[2-methyl-3-(4-amidinobenzoyl)carbazoyl] phenoxyacetate,
4-[2-methyl-3-(4-amidinobenzoyl)carbazoyl]phenoxyacetic acid and 4-[3-(4-phenylamidinobenzoyl)carbazoyl] phenoxyacetic acid;
or a pharmaceutically acceptable salt thereof.

A further specific especially preferred compound of the invention is the acid derivative of formula I being:
methyl 4-[3-(4-amidinobenzoyl)carbazoyl]phenoxyacetate;
or a pharmaceutically acceptable salt thereof.

The compounds of formula I, the metabolically labile esters and amides thereof, and the pharmaceutically acceptable salts thereof may be prepared by procedures analogous to procedures known in the art for the preparation of structurally analogous compounds. Such procedures are included as a further feature of the invention and include the following preferred procedures for the manufacture of a compound of the formula I in which $R^1$, $R^2$, $R^3$, $X^1$, Q, $X^2$ and G have any of the meanings defined above:

(A) For a compound of formula I in which G is carboxy, deprotecting a compound of formula VI in which $G^1$ is a carboxy protecting group.

$G^1$ may be any conventional carboxy protecting group that may be removed without interfering with other parts of the molecule. Examples of carboxy protecting groups include (1–6C)alkyl groups (such as methyl, ethyl, propyl or t-butyl), phenyl and benzyl, the phenyl moiety in any of which may optionally bear 1 or 2 of halogeno, (1–4C)alkyl, (1–4C)alkoxy or nitro.

The deprotection may be carried out using any one or more of the conventional reagents and conditions known in the art for converting carboxylic esters into carboxylic acids. Thus, for example, the deprotection may conveniently be performed by base catalysed hydrolysis, for example by using an alkali metal hydroxide such as lithium, potassium or sodium hydroxide, or a tertiary amine such as triethylamine, in the presence of water. The base catalysed hydrolysis may conveniently be performed in the presence of a solvent such as an alcohol, for example methanol or ethanol, or an ether such as tetrahydrofuran or dioxan. Alternatively the deprotection may be carried out by acid catalysed hydrolysis, for example using acetic acid or trifluoroacetic acid. Suitable solvents for the acid catalysed hydrolysis include alcohols such as those mentioned above, halogenated hydrocarbons such as dichloromethane, ethers such as anisole, and water. The temperature is conveniently in the range of from –10 to 100° C., for example from 10 to 50° C. When the alcohol residue is t-butyl, this may also conveniently be removed by heating, for example at a temperature in the range of from 80 to 150° C., alone or in the presence of a suitable diluent such as diphenyl ether or diphenyl sulphone.

It will be appreciated that a compound of formula I in which G represents carboxy and Q represents a group of formula IV or V wherein $Z^3$ represents a group of formula $X^2$—COOH may be prepared by this process starting from a compound of formula VI in which Q represents a group of formula IV or V and $Z^3$ represents a group of formula $X^2$—COOH or $X^2$—COOG$^1$.

(B) For a compound of formula I in which $R^1$ is a group of formula II and A is an aminomethyl or an amidino group, deprotecting a compound of formula VII in which $A^1$ is a protected aminomethyl or amidino group.

$A^1$ may be any conventional protected aminomethyl or amidino group that may be deprotected without interfering with other parts of the molecule. Examples of protecting groups include oxycarbonyl groups such as t-butoxycarbonyl and benzyloxycarbonyl.

The deprotection may be carried out using any one or more of the conventional reagents and conditions known in the art for removing amine protecting groups. A t-butoxycarbonyl group may be removed by hydrolysis, for example by acid catalysed hydrolysis using an acid such as trifluoroacetic acid. Suitable solvents include halogenated hydrocarbons such as dichloromethane. A benzyloxycarbonyl group may conveniently be removed, for example, by hydrogenation in the presence of a palladium catalyst such as palladium on charcoal. The temperature is conveniently in the range of from –10 to 100° C., for example from 10 to 50° C.

In some cases the reaction conditions required to perform process (A) are the same as those required to perform process (B). In such cases it is possible to perform processes (A) and (B) at the same time by starting with a compound having an appropriate carboxy protecting group and an appropriate protected aminomethyl or amidino group. Such a compound is represented by the formula VIII.

(C) Reacting a compound of formula IX, or a reactive derivative thereof, with a compound of formula X.

A suitable reactive derivative of an acid of the formula IX may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol or an alcohol such as 1-hydroxybenzotriazole (HOBT); an acyl azide, for example an azide formed by the reaction of the acid and an azide such as diphenylphosphoryl azide; or an acyl cyanide, for example a cyanide formed by the reaction of an acid and a cyanide such as diethylphosphoryl cyanide. The reaction may also conveniently be performed in the presence of a peptide coupling agent, for example a carbodiimide such as 1,3-dicyclohexylcarbodiimide (DCC) and 1-(3-dimethylaminopropyl)-3-ethylcarbodiimide, optionally in the presence of HOBT or O-benzotriazol-1-yl-N,N,N$^1$-, N$^1$-tetramethyluronium hexafluorophosphate (HBTU). The reaction is conveniently performed at a temperature in the range of from –10 to 100° C. Suitable solvents include ethers such as tetrahydrofuran and amides such as dimethylformamide.

(D) Reacting a compound of formula XI with a compound of formula XII, or a reactive derivative thereof.

Examples of reactive derivatives of compounds of formula XII include those mentioned hereinbefore for reactive derivatives of compounds of formula IX. The reaction is conveniently performed at a temperature in the range of from –10 to 100° C. Suitable solvents include ethers such as tetrahydrofuran and amides such as dimethylformamide.

(E) For a compound of formula I in which $X^2$ is a group of formula $CH_2CH(NHXR^4)$, reacting a compound of formula XIII in which $X^{2a}$ is $CH_2CH(NH_2)$, or an acid addition salt thereof, with a compound of formula XIV in which $U^1$ is a leaving atom or group.

Examples of values for $U^1$ include halogen such as chlorine or bromine and hydrocarbylsulphonyloxy such as methanesulphonyloxy and p-toluenesulphonyloxy. Examples of acid addition salt include for example, the hydrochloride. The reaction may conveniently be effected at a temperature in the range of from –10 to 120° C. preferably from 10 to 100° C. Suitable solvents include for example ethers such as tetrahydrofuran, amides such as dimethylformamide, nitriles such as acetonitrile, halogenated hydrocarbons such as dichloromethane and alcohols such as ethanol. The reaction is conveniently performed in the presence of a base, for example a tertiary amine such as triethylamine.

(F) For a compound of formula I in which $R^1$ is a group of formula II and A is a group of formula $R^aN=C(NH_2)-$, reacting a compound of formula XV, in which $U^2$ is a leaving atom or group, with a compound of formula $R^aNH_2$.

Examples of values for $U^2$ include (1–4C)alkylthio groups such as methylthio. Suitable media for the reaction include alcohols such as methanol or ethanol, and halogenated hydrocarbons such as dichloromethane. The reaction is conveniently performed at a temperature in the range of from –10 to 100° C.

(G) For a compound of formula I in which $X^1$ is a bond and Q is a group of formula V, reacting a compound of formula XVI, or a reactive derivative thereof, with a compound of formula XVII.

Examples of reactive derivatives of compounds of formula XVI include those mentioned hereinbefore for reactive derivatives of compounds of formula IX. The reaction is conveniently performed at a temperature in the range of from –10 to 100° C. Suitable solvents include ethers such as tetrahydrofuran and amides such as dimethylformamide.

The intermediates used in the aforementioned processes are either known or may be prepared by methods analogous to methods known for preparing known compounds. In general, the intermediates containing a carbazolyl group or an acylhydrazino group are prepared by reacting the appropriate hydrazine derivative with the appropriate carboxylic acid, or a reactive derivative thereof, using a conventional peptide coupling method.

Thus, the compounds of formula VI may be prepared by reacting a compound of formula XVIII with a compound of formula IX, or a reactive derivative thereof, by a method analogous to that of process (C) described hereinabove. Alternatively, the compounds of formula VI may be prepared by reacting a compound of formula XIX, or a reactive derivative thereof, with a compound of formula XI by a method analagous to that of process (D) described hereinabove.

The compounds of formula VI in which $R^1$ is a group of formula II and A is an aminomethyl group may also be prepared by selectively deprotecting a compound of formula VIII. Similarly, the compounds of formula VII may also be prepared by selectively deprotecting a compound of formula VIII.

The compounds of formula VIII may be prepared by reacting a compound of formula XX, or a reactive derivative thereof, with a compound of formula XVIII following a method analogous to that of process (C) described hereinabove. Alternatively they may be prepared by reacting a compound of formula XXI with a compound of formula XII, or a reactive derivative thereof, following a method analogous to that of process (D) described hereinabove.

The compounds of formula X may be prepared by reacting a compound of formula $HNR^2NR^3H$, or a protected derivative thereof (for example an N-benzyloxycarbonyl or N-t-butoxycarbonyl derivative), with a compound of formula XII, or a reactive derivative thereof, followed if necessary by removing any protecting group, for example by hydrogenation in the presence of palladium on carbon. Similarly, the compounds of formula XI may be prepared by reacting a compound of formula $HNR^2NR^3H$, or a protected derivative thereof (for example an N-benzyloxycarbonyl or N-t-butoxycarbonyl derivative), with a compound of formula IX, or a reactive derivative thereof, followed if necessary by removing any protecting group, for example by hydrogenation in the presence of palladium on carbon.

The compounds of formula XIII may be prepared by a method analogous to process (D), but using a compound of formula XXII, or a reactive derivative thereof, or an N-protected derivative thereof, instead of a compound of formula XII, and if necessary removing the protecting group.

The compounds of formula XV in which $U^2$ is a (1–4C) alkylthio group may be prepared by reacting a compound of formula XXIII with an alkylating agent, for example a (1–4C)alkyl halide such as methyl iodide.

The compounds of formula XXIII may be prepared by reacting a compound of formula XXIV with hydrogen sulphide.

The compounds of formula XXIV may be prepared by reacting a compound of formula XXV, or a reactive derivative thereof, with a compound of formula X.

The compounds of formula XVI may be prepared by reacting a compound of formula XXVI, or a protected derivative thereof (such as a benzyl ester), with a compound of formula IX, or a reactive derivative thereof, followed if necessary by the removal of the protecting group (for example, by hydrogenolysis).

The compounds of formula XXI may be prepared by reacting a compound of formula XX, or a reactive derivative thereof, with a compound of formula $HNR^2NR^3H$.

The compounds of formula XVIII may be prepared by reacting a compound of formula XIX, or a reactive derivative thereof, with a compound of formula $HNR^2NR^3H$, or a protected derivative thereof, followed if necessary by removing the protecting group.

The compounds of formula I may be converted into pharmaceutically acceptable salts and/or metabolically labile esters or amides thereof by methods well known in the art. For example, a pharmaceutically acceptable salt may be formed by reacting a compound of formula I with an acid capable of affording a physiologically acceptable anion, or a base capable of affording a physiologically acceptable cation. A pharmaceutically acceptable metabolically labile ester or amide may be formed respectively by esterifying a compound of formula I using a conventional technique, or reacting an acid, or a reactive derivative thereof, with an appropriate amine. Similarly, when an optically active form of a chiral compound of formula I is required, either one of processes (A)–(G) above may be carried out using the appropriate optically active starting material or else a racemic form may be resolved by a conventional procedure, for example, using an optically active form of a suitable acid.

Many of the intermediates, for example compounds of formulae VI, VII, VIII, XIII, XV, XXIII and XXIV are novel and form further aspects of this invention.

The ability of the compounds of formula I to inhibit platelet aggregation may be demonstrated using a standard test (a) based on that described by Born (*Nature,* 1962, 194, 927–929) and involving:

(i) aggregating human, citrated, platelet-rich plasma by addition of adenosine diphosphate (ADP) so as to generate a dose-response curve;
(ii) generating a dose-response curve for ADP stimulated platelet aggregation in the presence of increasing amounts of a test compound (generally in the range $10^{-5}$M to $10^{-10}$M); and
(iii) calculating a $pA_2$ value indicating potency of platelet aggregation inhibition for the test compound, averaged over several concentrations, from the calculated 50% response value for ADP aggregation in the presence and absence of the test compound.

Test (a) may be modified so as to assess the effects of a test compound ex vivo on the aggregation of human blood platelets after administration of the test compound to a laboratory animal, such as a rat, rabbit, guinea pig, mouse or dog. For example, groups of fourmale, fasted Alderley Park Wistar rats are orally dosed with a test compound or appropriate vehicle, and at suitable time intervals (1, 3, 5 and 8 hours after dosing) animals are anaesthetised with fluothane and bled by heart puncture. Blood is collected into 3.2% citrate (1 part to 9 parts whole blood) and platelet poor plasma (ppp) prepared by centrifugation (4500× g for 10 minutes).

Human blood is collected into 3.2% trisodium citrate (1 part to 9 parts whole blood) and centrifugated (200× g for 15 minutes) to produce platelet rich plasma (prp).

Equal volumes (125 µl) of rat ppp and human prp are mixed together, ADP added, and the whole incubated (37° C.) and stirred (900 rpm) in a BioData platelet aggregometer. Aggregation is induced with ADP and agonist $EC_{50}$ values calculated for human prp/rat ppp mixtures from animals dosed with test compound or vehicle. A mean concentration ratio (concentration of ADP required to cause a 50% aggregation response in human prp/rat ppp mixtures from animals dosed with antagonist, divided by the concentration of ADP to cause 50% aggregation in human prp/rat ppp mixtures from animals dosed with vehicle) is calculated at each time point.

The ability of the compounds of formula I to inhibit binding of fibrinogen to GPIIb-IIIa may be demonstrated using the following standard test (b) involving:
(i) Preparation of human platelet lysates.
Platelet rich plasma (prp) is harvested by centrifugation (1000 rpm, 15 minutes) of whole blood anticoagulated with acid citrate dextrose (trisodium citrate 85 mM, citric acid 70 mM, d-glucose 110 mM), 1 part to 6 parts blood. Prostacyclin ($PGI_2$, 1 µM) is added to the prp before centrifugation (2400 rpm, 15 min) and the resulting pellet is resuspended in modified Tyrodes' solution (NaCl 130 mM, KCl 26 mM, $NaHCO_3$ 12mM, $NaH_2PO_4$ 0.5 mM, $MgCl_2$ 1 mM, $CaCl_2$ 20 mM, Glucose 12 mM, HEPES 5 mM) containing bovine serum albumin 3.5 g/L, $PGI_2$ 1 µM and hirudin 0.5 U/ml. The platelet suspension is centrifuged (2400 rpm, 15 minutes) and the resultant pellet resuspended in 500 µl of lysis buffer (octyl glucoside 50 mM, HEPES 10 mM, NaCl 150 mM, $CaCl_2$ 1 mM, $MgCl_2$ 1 mM, PMSF 1 mM, NEM 10 mM, leupeptin 0.1 mM), agitated at 4° C. for 15 minutes then centrifuged at 24000 rpm, 15 minutes. The supernatant is stored at 4° C. and the pellet re-suspended in 500 µl of lysis buffer. The centrifugation process is repeated a further 3 times, the pooled supernatants being stored at −70° C.
(ii) Receptor purification.
Glycoprotein IIb/IIIa is isolated from human platelet lysates using a 2 ml peptide (KYGRGDS) coupled CNBr activated Sepharose affinity column. A 1.5 ml volume of platelet lysate is placed on the column and allowed to stand overnight at 4° C. Buffer (30 ml, octyl glucoside 25 mM, HEPES 10 mM, NaCl 150 mM, $CaCl_2$ 1 mM, $MgCl_2$ 1 mM, PMSF 1 mM, NEM 10 mM, leupeptin 0.1 mM) is passed through the column and 2 ml fractions are collected throughout. GPIIb/IIIa is eluted with 12 ml of buffer containing HHLG-GAKQAGDV (2 mg/ml, pH7.5), the column is washed using 4 ml buffer and the remaining GPIIb/IIIa eluted using 12 ml buffer containing GRGDSPG (1 mg/ml pH7.5). The column is finally washed using 20 ml of buffer and can be used for up to three such preparations. Fractions containing GPIIb/IIIa are identified using gel electrophoresis and immunoblotting, pooled and stored at −70° C.
(iii) GPIIb/IIIa ELISA
96 well microtitre plates are coated with 100 µl purified human platelet fibrinogen receptor (GPIIb/IIIa) diluted in coating buffer (Tris-HCl 20 mM, NaCl 150 mM, $CaCl_2$ 1 mM, pH7.4) and left overnight at 4° C. The plates are washed using washing buffer (Tris-HCl 50 mM, NaCl 100 mM, $CaCl_2$ 2 mM, pH7.4) and non-specific binding blocked by the addition of 200 µl 2% BSA (2 hours, 30° C.). The plates are washed prior to incubation (2 hours, 30° C.) with 100 µl biotinylated fibrinogen (10 nM) containing either vehicle or test compound. The plates are washed, incubated with streptavidin (5 µg/ml, 1 hour, ambient temperature), then washed again before the addition of 100 µl biotinylated horse radish peroxidase (0.1 µg/ml, 1 hour, ambient temperature). The plates are then washed and equal volumes of peroxidase substrate (3,3',5,5'-tetramethylbenzidine 0.4 g/l) and $H_2O_2$ (0.02%) are mixed together immediately before addition of 150 µl to each well. Colour is allowed to develop for 10–15 minutes before optical densities are read at 650 nm.

Abbreviations
PMSF Phenylmethylsulphonyl fluoride
HEPES 2-[4-(2-hydroxyethyl)piperazin-1-yl]ethanesulphonic acid
NEM N-ethylmaleimide The concentration of compound required to cause 50% inhibition of biotinylated fibrinogen binding is calculated and expressed as a $pIC_{50}$ ($-\log(IC_{50})$).

The compounds of formula I exemplified herein have been found to show effects in the following ranges in at least one of the above tests:
test (a): $pA_2$ of >4.5
test (b): $pIC_{50}$ of >4.5

In general, it has been found that compounds of formula I in which G is carboxy show a higher level of activity in test (a) and test (b) than those in which G is an ester group. However, the compounds in which G is an ester group in general have been found to show a higher level of activity than those where G is carboxy in test (a) when the test is modified to assess the activity of test compounds on oral administration For example, the compound described in Example 12 hereinafter has been found to give a $pA_2$ of 6.7 in test (a) and a $pIC_{50}$ of 5.95 in test (b), whereas the compound of Example 13 has been found to give a $pA_2$ of 8.1 in test (a) and a $pIC_{50}$ of 7.8 in test (b). However, the compound of Example 12 has been found to be active for up to 24 hours when dosed orally to dogs at 3 mg/kg. Without wishing to be bound by theory it is accordingly believed that the compounds of formula I in which G represents an ester group function as pro-drugs for compounds of formula I in which G is a carboxy group.

As stated previously, the compounds of formula I may be used in the therapy or prevention of diseases in which cell adhesion (especially platelet aggregation) is involved, for example venous or arterial thrombosis (for example pulmonary embolism, stroke and thrombotic events accompanying unstable angina and transient ischaemic attack), myocardial infarction, migraine, atherosclerosis, thromboembolism and reocclusion during and after thrombolytic therapy. The compounds may also be useful for the prevention of reocclusion or restenosis following percutaneous transluminal coronary angioplasty (PTCA) and coronary artery bypass graft. It will also be appreciated that the compounds may be useful in the treatment of other diseases mediated by binding of adhesion molecules to GPIIb/IIIa, for example cancer.

According to another aspect, therefore, the invention provides a method of inhibiting platelet aggregation in a warm-blooded mammal requiring such treatment, which comprises administering an effective amount of a compound of formula I, or a pharmaceutically acceptable metabolically labile ester or amide thereof, or a pharmaceutically acceptable salt thereof.

According to yet another aspect, the invention provides a method of inhibiting binding of fibrinogen to GPIIb/IIIa in a warm-blooded animal requiring such treatment, which comprises administering an effective amount of a compound of formula I, or a pharmaceutically acceptable metabolically labile ester or amide thereof, or a pharmaceutically acceptable salt thereof.

According to a further aspect, the invention provides the use of a compound of formula I, or a pharmaceutically acceptable metabolically labile ester or amide thereof, or a pharmaceutically acceptable salt thereof, for the manufacture of a medicament for the prevention or treatment of a disease involving platelet aggregation.

According to yet another aspect, the invention provides the use of a compound of formula I, or a pharmaceutically acceptable metabolically labile ester or amide thereof, or a pharmaceutically acceptable salt thereof, for the manufacture of a medicament for the prevention or treatment of a disease involving binding of fibrinogen to GPIIb/IIIa.

In general, a compound of formula I will be administered for this purpose by an oral, rectal, topical, intravenous, subcutaneous, intramuscular or inhalation route, so that a dose in the range of from 0.01 to 50 mg/kg body weight will be given, depending upon the route of administration, the age and sex of the patient, and the severity of the condition to be treated.

The compounds of formula I will generally be used in the form of a pharmaceutical composition comprising a compound of formula I, or a pharmaceutically acceptable metabolically labile ester or amide thereof, or a pharmaceutically acceptable salt thereof, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of creams or ointments or a transdermal (skin) patch for topical administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation. Depending upon the route of administration, the composition will, in general, comprise, for example, 1 to 99% by weight of a compound of formula I.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The compounds according to the invention may be co-adminstrated or co-formulated with one or more agents known to be of value in diseases or conditions intended to be treated; for example a known platelet aggregation inhibitor (e.g. aspirin, a thromboxane antagonist or a thromboxane synthase inhibitor), hypolipidemic agent, anti-hypertensive agent, thrombolytic agent (such as streptokinase, urokinase, prourokinase, tissue plasminogen activator and derivatives thereof), beta-adrenergic blocker or a vasodilator may usefully also be present in a pharmaceutical composition of the invention for use in treating a heart or vascular disease or condition.

In addition to their use in therapeutic medicine, the compounds of formula I are also useful as pharmacological tools in the development and standardisation of test systems for the evaluation of the effects of adhesion molecules in laboratory animals such as cats, dogs, rabbits, monkeys, rats and mice, as part of the search for new therapeutic agents. The compounds of formula I may also be used because of their platelet aggregation inhibitory properties in helping to store blood and to maintain the viability of blood and blood vessels in warm-blooded animals (or parts thereof) undergoing artificial extracorporeal circulation, for example during limb or organ transplants. When used for this purpose a compound of formula I, or a pharmaceutically acceptable salt thereof, will generally be administered so that a steady state concentration in the range, for example, 0.1 to 10 mg per liter is achieved in the blood.

The invention will now be illustrated by the following non-limiting Examples in which unless otherwise stated:

(i) concentrations and evaporations were carried out by rotary evaporation in vacuo;

(ii) operations were carried out at ambient temperature, that is, in the range 18–26° C.;

(iii) column chromatography was carried out on silica (Merck Art. 9385) available from E Merck and Co., Darmstadt, Germany;

(iv) yields are given for illustration only and are not necessarily the maximum attainable by diligent process development;

(v) proton NMR spectra were normally determined at 200 MHz or 250 MHz in dimethylsulphoxide-$d_6$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and (vi) ether refers to diethyl ether, THF to tetrahydrofuran, DMF to N,N-dimethylformamide, TFA to trifluoroacetic acid; DMSO to dimethylsulphoxide; HOBT to 1-hydroxybenzotriazole hydrate; and HBTU to O-benzotriazol-1-yl-N,N,$N^1$,N -tetramethyluronium hexafluorophosphate.

EXAMPLE 1

1-[3-(4-Aminomethylbenzoyl)carbazoyl]piperidin-4-yl-oxyacetic Acid, Trifluoroacetic Acid Salt A mixture containing t-butyl 1-[3-(4-t-butoxycarbonylaminomethyl-benzoyl)carbazoyl]piperidin-4-yloxyacetate (300 mg), TFA (10 ml) and dichloromethane (10 ml) was allowed to stand for 1.5 hours. The mixture was concentrated, treated with dichloromethane (10 ml) and concentrated again. The residue was treated with ether (10 ml) and concentrated. The resulting foam was crystallised from isopropanol (approximately 12 ml) to give the title compound (200 mg) as colourless prisms; m.p. 188–190° C.; NMR Spectrum 1.3–1.5 (2H, m); 1.7–1.9 (2H, m); 2.9–3.1 (2H, m); 3.55 (1H, m); 3.65–3.8 (2H, m); 4.05 (2H, s); 4.1 (2H, s); 7.55 (2H, d); 7.9 (2H, d); 8.0–8.5 (2H, br s); 8.6 (1H, s); 10.05 (1H, s).

The required starting material was prepared as follows:

(a) A solution containing 4-t-butoxycarbonylaminomethylbenzoic acid (5.0 g) and triethylamine (3.0 ml) in dry THF (180 ml) was treated at 10° C. with isobutyl chloroformate (2.7 ml) and the resulting mixture was stirred for 10 minutes. A solution of benzyl carbazate (3.4 g) in THF (20 ml) was added and the mixture was stirred for 15 hours at ambient temperature. The resulting precipitate was removed by filtration and the filtrate was diluted with ethyl acetate (500 ml) and washed with water (3×100 ml) and with saturated brine (100 ml). The organic solution was dried ($MgSO_4$) and evaporated to a volume of 150 ml. After 1 hour the mixture was filtered to give benzyl 3-(4-t-butoxycarbonylaminomethylbenzoyl)carbazate (3.6 g) as colourless prisms; m.p. 160–162° C.; NMR Spectrum 1.4 (9H, s); 4.2 (2H, d); 5.1 (2H, s); 7.2–7.5 (2H+5H, m); 7.8 (2H, d); 9.3 (1H, s); 10.3 (1H, s).

(b) A solution of the product of step (a) (5.7 g) in methanol (120 ml) was hydrogenolysed over 10% palladium on carbon (0.5 g) until hydrogen uptake ceased (1 hour). Activated charcoal was added and the mixture was stirred, filtered through diatomaceous earth and concentrated to give 4-(t-butoxycarbonylaminomethyl)benzoylhydrazine (3.6 g) as a colourless solid; m.p. (from toluene) 114–116° C.; NMR Spectrum 1.4 (9H, s); 3.2–4.0 (2H, br s); 4.2 (2H, s); 7.3 (2H, d); 7.4 (1H, t); 7.8 (2H, d); 9.7 (1H, s).

(c) A solution of p-nitrophenyl chloroformate (2.5 g) in dry THF (40 ml) was treated dropwise at 0–5° C. with a solution containing the product of step (b) (3.0 g) and triethylamine (1.7 ml) in THF (60 ml) and the mixture was stirred at ambient temperature for 2 hours. Ethyl acetate (100 ml) was added and the solution was extracted with water (3×100 ml) and with saturated brine (100 ml), dried ($MgSO_4$) and concentrated. The residue was purified by column chromatography on silica, eluting with hexane/ether (60% then 50% then 40%) to give 5-(4-t-butoxycarbonylaminomethyl)phenyl-2(3H)-1,3,4-oxadiazolone (2.5 g as a colourless solid; m.p. (from toluene) 152–154° C.; NMR Spectrum 1.4 (9H, s); 4.2 (2H, d); 7.4 (2H, d); 7.45 (1H, t); 7.75 (2H, d); 12.5 (1H, s).

(d) A solution containing 4-piperidinol (5 g) and triethylamine (7 ml) in dichloromethane (50 ml) was treated with benzyl chloroformate (7.5 ml), added dropwise, and the resulting mixture was allowed to stand for 2 hours. The mixture was diluted with dichloromethane (50 ml) and washed with water (2×50 ml) and with saturated brine (50 ml). The organic solution was dried ($MgSO_4$) and concentrated. The residue was purified by column chromatography, eluting with ether/hexane (50%, then 75%) followed by ether, to give 1-(benzyloxycarbonyl)piperidin-4-ol (7.5 g) as a colourless oil; NMR Spectrum 1.2–1.4 (2H, m); 1.6–1.8 (2H, m); 3.0–3.2 (2H, m); 3.6–3.8 (3H, m); 4.7 (1H, d); 5.05 (2H, s); 7.3–7.4 (5H, m).

(e) Sodium hydride (60% dispersion in mineral oil, 1.3 g) was added to a stirred solution of the product of step (d) (7 g) and the mixture was stirred until effervescence ceased. t-Butyl bromoacetate (5.1 ml) was added and the mixture was stirred for 2 hours. The mixture was diluted with ether (200 ml) and washed with water (3×100 ml) and with saturated brine (100 ml). The organic solution was dried ($MgSO_4$) and concentrated. The residue was purified by column chromatography, eluting with ether/hexane (50%) then ether, to give t-butyl 1-(benzyloxycarbonyl)piperidin-4-yloxyacetate (3.0 g) as a colourless oil; NMR Spectrum 1.3–1.5 (2H, m); 1.4 (9H, s); 1.7–1.9 (2H, m); 3.0–3.2 (2H, m); 3.5–3.6 (1H, m); 3.6–3.8 (2H, m); 4.0 (2H, s); 5.05 (2H, s); 7.3–7.4 (5H, m).

(f) A solution of the product of step (e) (1.0 g) in isopropanol (40 ml) was treated with activated charcoal, filtered and hydrogenolysed over 10% palladium on charcoal (200 mg). When hydrogen uptake had ceased, the mixture was filtered and concentrated to give t-butyl piperidin-4-yloxyacetate (620 mg) as a colourless oil which solidified on standing in the freezer and which was used without characterisation.

(g) A mixture comprising the product of step (f) (620 mg), the product of step (c) (750 mg) and acetonitrile (25 ml) was heated to reflux for 5 hours. The mixture was concentrated and the residue was purified by silica column chromatography, eluting with dichloromethane/methanol (98:2) to give a foam, which, on crystallisation from tetrachloromethane (approximately 16 ml), gave t-butyl 1-[3-(4-t-butoxycarbonylaminomethybenzoyl)carbazoyl]piperidin-4-yloxyacetate (600 mg) as colourless prisms; m.p. 104–106° C.; NMR Spectrum 1.3–1.35 (9H, s; 9H, s; 2H, m); 1.7–1.9 (2H, m); 2.9–3.1 (2H, m); 3.5–3.6 (1H, m); 3.6–3.8 (2H, m); 4.0 (2H, s); 4.15 (2H, d); 7.3 (2H, d); 7.4 (1H, t); 7.8 (2H, d); 8.55 (1H, s); 10.0 (1H, s).

EXAMPLE 2

4-[3-(4-Piperidinylcarbonyl)carbazoyl]-2-(carboxymethoxy)phenoxyacetic Acid, Trifluoroacetate Salt A mixture of t-butyl 4-[3-(1-t-butoxycarbonyl-piperidin-4-ylcarbonyl)-carbazoyl]-2-(t-butoxycarbonylmethoxy) phenoxyacetate (360 mg) and TFA (4 ml) in dichloromethane (8 ml) was stirred at ambient temperature for 5 hours. The solvent was removed by evaporation and the residue was triturated with ether to give the title compound as a solid; NMR Spectrum ($d_6$-DMSO) 1.68–2.02 (m, 4H), 2.55–2.68 (m, 1H), 2.85–3.05 (dt, 2H), 3.2–3.4 (br d, 2H), 4.74 (s, 2H), 4.78 (s, 2H), 6.97 (d, 1H), 7.4 (s, 1H), 7.47 (dd, 1H), 8.5 (br s, 2H), 9.9 (s, 1H), 10.2 (s, 1H); Mass Spectrum (+ve FAB, MeOH/NBA): 396 $(M+H)^+$.

The starting material was prepared as follows:

(a) A solution of sodium hydroxide (6.4 g) in water (40 ml) was added to a mixture of 3,4-dihydroxybenzoic acid (24.8 g) and DMF (200 ml) which had been cooled in an ice-bath. The mixture was stirred for 20 minutes and then benzyl bromide (19.1 ml) was added dropwise. After the addition was complete, the mixture was allowed to reach ambient temperature and was stirred for 20 hours. The mixture was then warmed to 50° C. for 2 hours. The solvent was removed by evaporation and the residue was partitioned between water (300 ml) and ethyl acetate (100 ml). The ethyl acetate layer was separated and the aqueous layer extracted with ethyl acetate (100 ml). The combined ethyl acetate extracts were washed with water (100 ml), saturated sodium hydrogen carbonate solution (100 ml), water (100 ml) and with saturated sodium chloride solution (100 ml) and dried ($MgSO_4$). The solvent was removed by evaporation to give a brown solid which was crystallised from toluene to give benzyl 3,4-dihydroxybenzoate (19 g) as a solid; m.p. 147–149° C.

(b) Sodium hydride (6.55 g, 60% dispersion in mineral oil) was washed with hexane (2×75 ml) and suspended in DMF (80 ml). The mixture was cooled to 10° C. and the product of step (a) (19 g) in DMF (100 ml) was added dropwise during 20 minutes keeping the temperature between 10–15° C. After the addition, the mixture was stirred for 40 minutes at ambient temperature and then cooled to 10° C. and t-butyl bromoacetate (25.2 ml) was added dropwise. The mixture was stirred for 4 hours at ambient temperature. The solvent was removed by evaporation, ice-water (300 ml) was added to the residue and the mixture was extracted with diethyl ether (2×200 ml). The combined extracts were washed with water (3×100 ml) and saturated sodium chloride solution (100 ml) and dried (MgSO$_4$). The solvent was removed by evaporation to give benzyl 3,4-di-t-butoxycarbonylmethoxybenzoate (35.5 g) as an oil; NMR Spectrum (CDCl$_3$) 1.45 (s, 9H), 1.47 (s, 9H), 4.62 (s, 2H), 4.65 (s, 2H), 5.32 (s, 2H), 6.81 (d, 1H), 7.4 (m, 5H), 7.52 (d, 1H), 7.7 (dd, 1H).

(c) A mixture of a solution of the product of step (b) (34.6 g) in ethyl acetate (600 ml) and 10% palladium/carbon (3 g) was stirred under an atmosphere of hydrogen for 5 hours at ambient temperature. The mixture was filtered through a pad of kieselguhr and the solvent was removed by evaporation to give a solid residue which was crystallised from ethyl acetate/hexane to give 3,4-di-t-butoxycarbonylmethoxybenzoic acid; m.p. 118–120° C.; NMR Spectrum (d$_6$-DMSO) 1.41 (s, 18H), 4.7 (s, 2H), 4.76 (s, 2H), 6.95 (d, 1 H), 7.39 (m, 1H), 7.55 (dd, 1H); Microanalysis found: C, 59.5; H, 6.8%; C$_{19}$H$_{26}$O$_8$ requires C, 59.7; H, 6.9%.

(d) 1-(3-Dimethylaminopropyl)-3-ethylcarbodiimide hydrochloride (1.92 g) was added to a mixture of the product of step (c) (3.82 g), HOBT (1.71 g), diisopropylethylamine (1.75 ml) and DMF (30 ml) at ambient temperature and stirred for 30 minutes. Benzyl carbazate (1.66 g) in DMF (10 ml) was added and the mixture was stirred for 20 hours at ambient temperature. The solvent was removed by evaporation. The residue was dissolved in ethyl acetate (160 ml) and the solution was washed with 1M citric acid solution (25 ml), water (2×25 ml), 1M sodium hydroxide solution (20 ml), water (25 ml) and with saturated sodium chloride solution (25 ml) and dried (MgSO$_4$). The solvent was removed by evaporation to give benzyl 3-(3,4-di-t-butoxycarbonylmethoxybenzoyl)carbazate as a gum; NMR Spectrum (d$_6$-DMSO) 1.43 (s, 18H), 4.70 (s, 2H), 4.75 (s, 2H), 5.11 (s, 2H), 6.96 (d, 1H), 7.34 (br s, 5H), 7.4 (d, 1H), 7.49 (dd, 1H), 9.28 (br s, 1H), 10.17 (br s, 1H); Mass Spectrum (+ve FAB, DMSO/GLYCEROL) 530 (M+H)$^+$.

(e) A mixture of a solution of the product of step (d) (5.3 g) in ethanol (150 ml) and 10% palladium/carbon (1 g) was stirred in a stream of hydrogen for 4 hours. The mixture was filtered through a pad of kieselguhr and the solvent was removed by evaporation to give t-butyl 2-t-butoxycarbonylmethoxy-4-carbazoylphenoxyacetate as a gummy residue (3.9 g). 1-(3-Dimethylaminopropyl)-3-ethylcarbodiimide hydrochloride (290 mg) was added to a stirred mixture of 1-t-butoxycarbonylpiperidine-4-carboxylic acid (345 mg), 1-hydroxybenztriazole (260 mg) and diisopropylethylamine (0.26 ml) and DMF (4 ml) at ambient temperature. The mixture was stirred for 20 minutes. A solution of a portion (600 mg) of the gummy residue in DMF (3.5 ml) was added and the mixture was stirred for 2.5 days. The solvent was removed by evaporation and the residue was partitioned between ethyl acetate (50 ml) and water (10 ml) and 1M citric acid solution (2 ml). The ethyl acetate extract was washed with water (10 ml), 0.25M sodium hydroxide solution (10 ml), water (10 ml) and saturated sodium chloride solution (10 ml) and dried (MgSO4). The solvent was removed by evaporation and the residue was purified by column chromatography eluting with ethyl acetate/dichloromethane (1:1 by volume) to give t-butyl 4-[3-(1-t-butoxycarbonyl-piperidin-4-yl-carbonyl) carbazoyl]-2-(t-butoxycarbonylmethoxy)phenoxyacetate (370 mg) as an amorphous solid; NMR Spectrum (d$_6$-DMSO) 1.3–1.5 (m, 29H), 1.68 (m, 2H), 2.38 (m, 1H), 2.72 (t, 2H), 3.9 (d, 2H), 4.65 (s, 2H), 4.7 (s, 2H), 6.9 (d, 1H), 7.38 (d, 1H), 7.43 (dd, 1H), 9.78 (s, 1H), 10.09 (s, 1H).

EXAMPLES 3–7

Using an analogous deprotection procedure to that described in Example 2, the following compounds were obtained:

EXAMPLE 3

4-[3-(3-Piperidin-4-ylpropanoyl)carbazoyl]-2-(carboxymethoxy)phenoxyacetic Acid, Trifluoroacetic Acid Salt NMR Spectrum (d$_6$-DMSO) 1.24 (m, 2H), 1.52 (m, 2H), 1.83 (d, 2H), 2.21 (t, 2H), 2.82 (t, 2H), 3.25 (d, 2H), 4.71 (s, 2H), 4.74 (s, 2H), 6.95 (d, 2H), 7.4 (d, 1H), 7.46 (dd, 1H), 8.52 (br s, 2H), 9.79 (s, 1H), 10.14 (s, 1H); Mass Spectrum (+ve FAB, MeOH/GLY) 424 (M+H)$^+$; Microanalysis found: C, 48.4; H, 5.7; N, 7.8%; C$_{19}$H$_{25}$N$_3$O$_8$.CF$_3$CO$_2$H.0.5 Et$_2$O requires: C, 48.1; H, 5.4; N, 7.3%.

The starting material was prepared as follows:

(a) Di-t-butyl dicarbonate (8 g) was added to a stirred mixture of 3-piperidin-4-ylpropionic acid hydrochloride (4 g), 0.5M sodium hydroxide solution (100 ml) and t-butanol (25 ml). The mixture was stirred at ambient temperature for 20 hours. The solvent was removed by evaporation and the residue was diluted with water (50 ml) and extracted with hexane (100 ml). The aqueous layer was separated, acidified with 10% potassium hydrogen sulphate solution to pH4 and extracted with ethyl acetate (2×75 ml). The combined ethyl acetate extracts were washed with saturated sodium chloride solution (25 ml) and dried (MgSO$_4$). The solvent was removed by evaporation to give 3-(1-t-butoxycarbonylpiperidin-4-yl)propionic acid as a solid; NMR Spectrum (d$_6$-DMSO) 0.8–1.1 (m, 2H), 1.25–1.5 (m, 12H), 1.6 (br d, 2H), 2.22 (t, 2H), 2.62 (t, 2H), 3.9 (br d, 2H); Mass Spectrum (CI$^+$, ACE) 258 (M+H)$^+$.

(b) 1-(3-Dimethylaminopropyl)-3-ethylcarbodiimide hydrochloride (380 mg) was added to a mixture of the product of step (a) (0.5 g), diisopropylethylamine (0.34 ml), 1-hydroxybenztriazole (333 mg) and DMF (10 ml) at ambient temperature. The mixture was stirred for 5 minutes and benzyl carbazate (325 mg) in DMF (2 ml) was added. The mixture was stirred for 18 hours at ambient temperature. The solvent was removed by evaporation and the residue was partitioned between ice-water (25 ml) containing 1M sodium hydroxide (2 ml) and ethyl acetate (50 ml). The ethyl acetate extract was washed with water (20 ml), 0.25M citric acid solution (20 ml), water (20 ml) and saturated sodium chloride solution (10 ml) and dried (MgSO$_4$). The solvent was removed by evaporation to give benzyl 3-[3-(1-t-butoxy-carbonylpiperidin-4-yl)propanoyl]carbazate as a foam (790 mg); NMR Spectrum (d$_6$-DMSO) 0.8–1.1 (m, 2H), 1.3–1.5 (m, 12H), 1.6 (br d, 2H), 2.1 (br t, 2H), 2.62 (m, 2H), 3.9 (br d, 2H), 5.07 (s, 2H), 7.32 (s, 5H), 9.08 (s, 1H), 9.6 (s, 1H).

(c) A mixture of a solution of the product of step (b) (780 mg) in ethanol (20 ml) and 10% palladium/carbon (200 mg)

was stirred in a stream of hydrogen at ambient temperature for 2 hours. The mixture was filtered through a pad of kieselguhr and the solvent was removed by evaporation to give a gum (520 mg) which was used without further purification. A solution of a portion (250 mg) of the gum in DMF (3 ml) was added to a stirred mixture of 3,4-di-t-butoxycarbonylmethoxybenzoic acid (360 mg), 1-hydroxybenztriazole (160 mg), diisopropylethylamine (0.16 ml), 1-(3-dimethylaminopropyl)-3-ethylcarbodiimide hydrochloride (180 mg) and DMF (10 ml) at ambient temperature. The mixture was stirred for 18 hours. The solvent was removed by evaporation and ice-water (10 ml) containing 1M sodium hydroxide solution (3 ml) was added to the residue which was extracted with ethyl acetate (50 ml). The ethyl acetate extract was washed with water (2×20 ml), 0.25M citric acid solution (20 ml), water (20 ml) and saturated sodium chloride solution (10 ml) and dried ($MgSO_4$). The solvent was removed by evaporation and the residue was purified by column chromatography eluting with ethyl acetate/dichloromethane (1:1) to give t-butyl 4-[3-[3-(1-t-butoxycarbonylpiperidin-4-yl)-propanoyl]carbazoyl]-2-(t-butoxycarbonylmethoxy)phenoxyacetate as a gum (330 mg); NMR Spectrum ($d_6$-DMSO) 0.85–1.1 (m, 2H), 1.3–1.6 (m, 30H), 1.69 (br d, 2H), 2.2 (t, 2H), 2.68 (br t, 2H), 3.94 (br d, 2H), 4.7 (s, 2H), 4.76 (s, 2H), 6.97 (d, 1H), 7.41 (d, 1H), 7.49 (dd, 1H), 9.8 (s, 1H), 10.12 (s, 1H).

EXAMPLE 4

4-[3-(2-Piperidin-4-ylacetyl)carbazoyl]-2-(carboxymethoxy)phenoxyacetic Acid, Trifluoroacetic Acid Salt NMR Spectrum ($d_6$-DMSO) 1.2–1.5 (m, 2H), 1.55–2.05 (m, 3H), 2.14 (d, 2H), 2.73–2.98 (br t, 2H), 3.25 (br d, 2H), 4.7 (s, 2H), 4.73 (s, 2H), 6.9 (d, 1H), 7.39 (dd, 1H), 7.43–7.58 (dd, 1H), 9.82 (s, 1H), 10.17 (s, 1H); Mass Spectrum (+ve FAB, MeOH/GLY) 410 $(M+H)^+$.

The starting material was prepared as follows:

(a) Di-t-butyldicarbonate (0.64 g) was added to a solution of ethyl 4-piperidinylacetate (0.5 g) in dichloromethane (5 ml) at ambient temperature and the mixture was stirred for 18 hours. The solvent was removed by evaporation and the residue was dissolved in a mixture of methanol (3 ml) and 2M sodium hydroxide solution (2 ml). The solution was allowed to stand at ambient temperature for 18 hours, diluted with water (50 ml) and extracted with diethyl ether (10 ml). The aqueous layer was acidified with 1H citric acid solution to pH4 and extracted with ethyl acetate (2×30 ml). The ethyl acetate extract was washed with water (10 ml) and saturated sodium chloride solution (10 ml) and dried ($MgSO_4$). The solvent was removed by evaporation to give 1-t-butoxycarbonyl-4-piperidineacetic acid as a solid (600 mg); NMR Spectrum ($d_6$-DMSO) 0.88–1.12 (m, 2H), 1.37 (s, 9H), 1.62 (br d, 2H), 1.7–1.9 (m, 1H), 2.13 (d, 2H), 2.69 (br t, 2H), 3.88 (d, 2H).

(b) Using a similar procedure to that described in Example 3, starting material steps (b) and (c) but starting from the product of step (a) immediately above, there was obtained t-butyl 4-[3-[2-(1-t-butoxy-carbonylpiperidin-4-yl)acetyl]carbazoyl]-2-(t-butoxycarbonylmethoxy)-phenoxyacetate; NMR Spectrum ($CDCl_3$) 1.08–1.3 (m, 2H), 1.45 (s, 9H), 1.49 (s, 9H), 1.50 (s, 9H), 1.74 (br d, 2H), 2.24 (d, 2H), 2.71 (br t, 2H), 4.1 (br d, 2H), 4.6 (s, 2H), 4.63 (s, 2H).

EXAMPLE 5

4-[3-(2-Piperidin-4-yloxyacetyl)carbazoyl]-2-(carboxymethoxy)phenoxyacetic Acid, Trifluoroacetic Acid Salt NMR Spectrum ($d_6$-DMSO) 1.7–2.05 (m, 2H), 2.9–3.1 (m, 2H), 3.1–3.3 (m, 2H), 3.6–3.9 (m, 3H), 4.08 (s, 2H), 4.75 (s, 2H), 4.79 (s, 2H), 6.98 (d, 1H), 7.42 (d, 1H), 7.44 (dd, 1H), 8.42 (br s, 2H), 9.8 (s, 1H), 10.2 (s, 1H); Mass Spectrum (+ve FAB, MeOH/NBA) 426 $(M+H)^+$.

The starting material was prepared as follows:

(a) Using a similar procedure to that described in Example 3, starting material step (a) but starting from piperidine-4-oxyacetic acid, there was obtained 1-t-butoxycarbonyl-4-piperidineoxyacetic acid; NMR Spectrum ($d_6$-DMSO) 1.27–1.5 (m, 11H), 1.7–1.88 (dd, 2H), 2.3–2.45 (m, 1H), 2.8 (t, 2H), 3.75–3.9 (m, 2H).

(b) Using a similar procedure to that described in Example 3, starting material steps (b) and (c) but starting from 1-t-butoxycarbonyl-4-piperidineoxyacetic acid, there was obtained t-butyl 4-[3-[2-(1-t-butoxycarbonyl)piperidin-4-yloxyacetyl]carbazoyl]-2-(t-butoxycarbonylmethoxy)phenoxyacetate as a gum; NMR Spectrum ($CDCl_3$) 1.46 (s, 9H), 1.47 (s, 9H), 1.48 (s, 9H), 1.5–1.7 (m, 2H), 1.75–1.98 (m, 2H), 3.02–3.2 (m, 2H), 3.5–3.68 (m, 1H), 3.7–3.88 (m, 2H), 4.17 (s, 2H), 4.65 (s, 2H), 4.67 (s, 2H), 6.83 (d, 1H), 7.4 (s, 1H), 7.43 (d, 1H), 8.89 (br d, 1H), 9.06 (br d, 1H).

EXAMPLE 6

4-[3-(3-Aminomethylbenzoyl)carbazoyl]-2-(carboxymethoxy)phenoxyacetic Acid, Trifluoroacetic Acid Salt NMR Spectrum ($d_6$-DMSO) 4.1 (s, 2H), 4.71 (s, 2H), 4.73 (s, 2H), 6.9 (d, 1H), 7.47 (s, 1H), 7.5–7.62 (m, 2H), 7.65 (d, 1H), 7.94 (d, 2H), 8.0 (s, 1H), 10.4 (br s, 2H); Mass Spectrum (+ve FAB, MeOH/NBA) 418 $(M+H)^+$.

The starting material was prepared as follows:

(a) Using a similar procedure to that described in Example 3, starting material step (b) but starting from 3-t-butoxycarbonylaminomethylbenzoic acid, there was obtained benzyl 3-t-butoxycarbonylaminomethylbenzoylcarbazate as a solid; NMR Spectrum ($d_6$-DMSO) 1.39 (s, 9H), 4.18 (d, 2H), 5.12 (s, 2H), 7.4 (m, 7H), 7.72 (m, 2H), 9.32 (s, 1H), 10.3 (s, 1H).

(b) Using a similar procedure to that described in Example 3, starting material step (c) but starting from the product of step (a) immediately above, there was obtained t-butyl 4-[3-(3-t-butoxycarbonylaminomethylbenzoyl)-carbazoyl]-2-(t-butoxycarbonylmethoxy)phenoxyacetate as a solid; NMR Spectrum ($d_6$-DMSO) 1.4 (s, 9H), 1.44 (s, 18H), 4.2 (br d, 2H), 4.73 (s, 2H), 4.78 (s, 2H), 7.0 (d, 2H), 7.46 (m, 4H), 7.56 (dd, 1H), 7.8 (m, 2H), 10.34 (br s, 1H), 10.41 (br s, 1H).

EXAMPLE 7

4-[3-(Piperazin-1-ylcarbonyl)carbazoyl]-2-(carboxymethoxy)phenoxyacetic Acid

NMR Spectrum ($d_6$-DMSO) 3.1 (br s, 4H), 3.63 (br t, 4H), 4.75 (s, 2H), 4.8 (s, 2H), 6.98 (d, 1H), 7.42 (d, 1H), 7.49 (dd, 1H), 8.81 (br s, 1H), 9.3 (br s, 2H), 10.03 (s, 1H); Mass Spectrum (+ve FAB, DMSO/NBA) 397 $(M+H)^+$.

The starting material was prepared as follows:

(a) A solution of 1,1-carbonyldiimidazole (435 mg) in dichloromethane (3 ml) was added to a stirred solution of benzyl carbazate (450 mg) in dichloromethane (2 ml) at ambient temperature. The mixture was stirred for 1 hour and a solution of 1-t-butoxycarbonylpiperazine (500 mg) in dichloromethane (3 ml) was added and the solution was left to stand for 2 weeks. The solvent was removed by evaporation and the residue was partitioned between ethyl acetate (60 ml) and water (15 ml). The ethyl acetate layer was washed with water (10 ml) and dried (MgSO$_4$). The solvent was removed by evaporation to give a solid which was crystallised from ethyl acetate to give benzyl 3-(4-t-butoxycarbonylpiperazin-1-ylcarbonyl)carbazate as a solid; m.p.194–196° C.; NMR Spectrum (d$_6$-DMSO) 1.41 (s, 9H), 3.28 (s, 8H), 5.06 (s, 2H), 7.35 (s, 5H), 8.56 (br s, 1H), 8.84 (br s, 1H); Mass Spectrum (+ve FAB, DMSO/NBA) 379 (M+H)$^+$.

(b) Using a procedure similar to that described in Example 2, starting material steps (c) and (d) but starting from the product of step (a) immediately above, there was obtained t-butyl 4-[3-(4-t-butoxy-carbonylpiperazin-1-ylcarbonyl)carbazoyl]-2-(t-butoxycarbonylmethoxy)phenoxyacetate; NMR Spectrum (d$_6$-DMSO) 1.42 (s, 9H), 1.43 (s, 18H), 3.35 (br s, 8H), 4.7 (s, 2H), 4.75 (s, 2H), 6.96 (d, 1H), 7.47 (d, 1H), 7.5 (dd, 1H), 8.63 (br s, 1H), 9.91 (br s, 1H).

EXAMPLE 8

4-[3-(4-Aminomethylbenzoyl)carbazoyl]-2-(carboxymethoxy)phenoxyacetic Acid, Trifluoroacetate Salt A solution of t-butyl 4-[3-(4-t-butoxycarbonylaminomethylbenzoyl)-carbazoyl]-2-(t-butoxycarbonylmethoxy)phenoxyacetate (100 mg) in a mixture of TFA (9 ml) and water (1 ml) was stored at ambient temperature for 2 hours. The reaction mixture was evaporated to near dryness and excess dry ether was added. The solvents were again removed in vacuo. The solid product was triturated with dry ether, collected and dissolved in 50% aqueous acetic acid (10 ml) with gentle warming. The solution was diluted with water (10 ml) and washed with ether (2×20 ml). The aqueous solution was filtered, diluted with water (20 ml) and lyophilised overnight to give the title compound (69 mg) as a white fluffy solid; NMR Spectrum (DMSO-d$_6$) 4.08 (2H, s), 4.60 (2H, s), 4.62 (2H, s), 6.95 (1H, m), 7.4–7.6 (4H, m), 7.92 (2H, m); Mass Spectrum m/Z 418 (M+H)$^+$;

The necessary starting material was prepared as follows:

(a) To a solution of the product of Example 2, starting material step (d) (270 mg), in methanol (20 ml) under argon was added 10% Pd on C (54 mg). The mixture was covered with a blanket of hydrogen and stirred at ambient temperature for 3.5 hours. The catalyst was filtered off through a pad of kieselguhr and washed with methanol (20 ml). The combined filtrate and washings were evaporated to dryness. To the oily residue was added a solution containing 4-t-butoxycarbonylaminomethylbenzoic acid (140 mg), HBTU (210 mg), HOBT (85 mg) and diisopropylethylamine (0.28 ml) in DMF (3 ml). The resultant pale yellow reaction mixture was stirred under a blanket of argon at ambient temperature overnight. The reaction mixture was diluted with ethyl acetate (20 ml) and washed with water, dilute KHSO$_4$ (aq.), dilute NaOH (aq.) and water, dried (MgSO$_4$) and evaporated. The crude product was precipitated from hot ethyl acetate by addition of hexane and finally recrystallised from aqueous methanol to give t-butyl 4-[3-(4-t-butoxycarbonylaminomethylbenzoyl)carbazoyl]-2-(t-butoxycarbonylmethoxy)phenoxyacetate (0.18 g) as an off-white solid; m.p. 156–158° C.; NMR Spectrum (DMSO-d$_6$) 1.40 (27H, br), 4.20 (2H, d), 4.72 (2H, s), 4.79 (2H, s), 7.00 (1H, d), 7.37 (2H, d), 7.88 (2H, d), 7.43 (1H, t), 7.49 (1H, d), 7.56 (1H, dd), 10.31 (1H, s), 10.38 (1H, s); Mass Spectrum m/Z 652 (M+Na)$^+$.

EXAMPLE 9

4-[3-Methyl-3-(4-aminomethylbenzoyl)carbazoyl]-2-(2-carboxymethoxy)phenoxyacetic Acid, Trifluoroacetate Salt In a similar manner to Example 8, t-butyl 4-[3-methyl-3-(4-t-butoxycarbonylaminomethylbenzoyl)carbazoyl]-2-(t-butoxycarbonylmethoxy)phenoxyacetate (480 mg) and 90% aqueous trifluoroacetic acid (50 ml) were reacted to give the title compound (356 mg) as a white fluffy freeze-dried solid; NMR Spectrum (D$_2$O) 3.56 (3H, s), 4.37 (2H, s), 4.88 (2H, s), 7.10 (2H, m), 7.37 (1H, dd), 7.68 (2H, d), 7.75 (2H, d); Mass Spectrum m/Z 432 (M+H)$^+$; Elemental Analysis: calculated for C$_{20}$H$_{21}$N$_3$O$_8$. 1.0 CF$_3$CO$_2$H. 0.5 H$_2$O: C, 47.7%; H, 4.2%; N, 7.6%; found: C, 47.8%; H, 4.3%; N, 7.6%.

The necessary starting material was prepared as follows:

(a) To a solution of the product of Example 2, starting material step (c) (470 mg), HBTU (460 mg) and HOBT (190 mg) in DMF (3 ml) under argon was added diisopropylethylamine (0.63 ml). After 2–3 minutes the resultant pale yellow reaction mixture was added to benzyl 2-methylcarbazate (Dutta, A. S. et al (1975), J. Chem. Soc. Perkin Trans. I, 1712–20) (200 mg). The reaction mixture was stirred at ambient temperature under argon for 3.5 hours then diluted with ethyl acetate (50 ml) and washed with water, dilute KHSO$_4$ (aq.) and dilute NaOH (aq.) and water, dried (MgSO$_4$) and evaporated to give benzyl 2-methyl-3-(3,4-di-t-butoxycarbonylmethoxybenzoyl)carbazate (0.61 g) as a glass; NMR Spectrum (DMSO-d$_6$) 1.43 (18H, s), 3.13 (3H, br s), 4.70 (2H, s), 4.75 (2H, s), 5.02–5.20 (2H, br), 6.99 (1H, m), 7.20–7.50 (7H, m), 10.68 (1H, br); Mass Spectrum m/Z 544 (M$^+$). In the ambient temperature NMR spectrum, ancillary signals attributable to rotamers were observed.

(b) To a solution of the product of step (a) (580 mg) in methanol (40 ml) under argon was added 10% Pd on C (120 mg). The mixture was covered with a blanket of hydrogen and stirred at ambient temperature for 3.5 hours. The catalyst was filtered off through a pad of kieselguhr and washed with methanol (40 ml). The combined filtrate and washings were evaporated to dryness. To the oily residue was added a solution containing 4-t-butoxycarbonylaminomethylbenzoic acid (300 mg), HBTU (460 mg), HOBT (190 mg) and diisopropylethylamine (0.62 ml) in DMF (10 ml). The resultant pale yellow reaction mixture was stirred under a blanket of argon at ambient temperature overnight. The reaction mixture was diluted with ethyl acetate (50 ml) and washed with water, dilute KHSO$_4$ (aq.), dilute NaOH (aq.), and with water, dried (MgSO$_4$) and evaporated. The residue was purified by column chromatography on silica, eluting with ethyl acetate/hexane, 2:1, to give t-butyl 4-[3-methyl-3-(4-t-butoxycarbonylaminomethylbenzoyl)-carbazoyl]-2-(t-butoxycarbonylmethoxy)phenoxyacetate (490 mg) as a glass; NMR Spectrum (DMSO-d$_6$) 1.37 (9H, s), 1.42 (18H, s), 3.19 (3H, s), 4.10 (2H, d), 4.67 (2H, s), 4.73 (2H, s), 6.92 (1H, d), 7.15–7.40 (5H, m), 7.48 (2H, m), 10.90 (1H, s); Mass Spectrum m/Z 666 (M+Na)$^+$.

EXAMPLE 10

4-[2-Methyl-3-(4-aminomethylbenzoyl)carbazoyl]-2-(2-carboxymethoxy)phenoxyacetic Acid, Trifluoroacetate Salt In a similar manner to Example 8, t-butyl 4-[2-methyl-3-(4-t-butoxycarbonylaminomethylbenzoyl)carbazoyl]-2-(t- butoxycarbonylmethoxy)phenoxyacetate (380 mg) and 90% aqueous TFA (40 ml) were reacted to give the title compound (289 mg) as a white fluffy freeze-dried solid; NMR Spectrum (DMSO-$d_6$+$CD_3CO_2D$) 3.24 (3H, s), 4.09 (2H, s), 4.66 (2H, s), 4.68 (2H, s), 6.85 (1H, d), 7.16 (2H, m), 7.50 (2H, d), 7.75 (2H, d), 11.6 (br, 4H); Mass Spectrum m/Z 432 (M+H)$^+$; Elemental Analysis: calculated for $C_{20}H_{21}N_3O_8$. 1.0 $CF_3CO_2H$. 0.5 $H_2O$: C, 47.7%; H, 4.2%; N, 7.6%; found: C, 47.8%; H, 4.6%; N, 7.6%.

The necessary starting material was prepared as follows:

(a) In a similar manner to Example 9, starting material step (a), 4-t-butoxycarbonylaminomethylbenzoic acid (300 mg), HBTU (460 mg), HOBT (190 mg), diisopropylethylamine (0.62 ml), DMF (3 ml) and benzyl 2-methylcarbazate (190 mg) were reacted to give benzyl 2-methyl-3-(4-t-butyoxycarbonylaminomethylbenzoyl)carbazate (440 mg) as a foam; NMR Spectrum (DMSO-$d_6$) 1.39 (9H, s), 3.13 (3H, s), 4.17 (2H, d), 5.08 (2H, s), 7.42 (8H, m), 7.78 (2H, m), 10.73 (1H, br); Mass Spectrum m/Z 414 (M+H)$^+$. In the NMR spectrum, ancillary signals attributable to rotamers were observed.

(b) In a similar manner to Example 9, starting material step (b), the product of step (a) (440 mg), 10% Pd on C (100 mg) and methanol (40 ml) were hydrogenolysed. A mixture of the oily residue so obtained, the product of Example 2, starting material step (c) (470 mg), HBTU (460 mg), HOBT (190 mg), diisopropylethylamine (0.63 ml) and DMF (3 ml) was reacted to give a residue which was purified by column chromatography on silica, eluting with ethyl acetate/hexane, 3:2, to give t-butyl 4-[2-methyl-3-(4-t-butoxycarbonylaminomethylbenzoyl)-carbazoyl]-2-(t-butoxycarbonylmethoxy)phenoxyacetate (380 mg) as a glass; NMR (DMSO-$d_6$) 1.33 (9H, s), 1.38 (9H, s), 1.43 (9H, s), 3.20 (3H, s), 4.13 (2H, d), 4.59 (2H, s), 4.67 (2H, s), 6.83 (1H, d), 7.13 (2H, m), 7.28 (2H, d), 7.62 (2H, d), 7.40 (1H, t), 10.98 (1H, s); Mass Spectrum m/Z 666 (M+Na)$^+$.

EXAMPLE 11

4-[2-Benzyl-3-(4-aminomethylbenzoyl)carbazoyl]-phenoxyacetic Acid, Trifluoroacetate Salt, and 4-[3-benzyl-3-(4-aminomethylbenzoyl)carbazoyl] phenoxyacetic Acid, Trifluoroacetate Salt, Approximately 4:1 Mixture In a similar manner to Example 8, a mixture of t-butyl 4-[2-benzyl-3-(4-t-butoxycarbonylaminomethylbenzoyl) carbazoyl]phenoxyacetate and t-butyl 4-[3-benzyl-3-(4-t-butoxycarbonylaminomethylbenzoyl)-carbazoyl] phenoxyacetate (120 mg) and 90% aqueous TFA (20 ml) gave the title mixture of compounds (116 mg) as a white fluffy freeze-dried solid; NMR Spectrum (DMSO-$d_6$ of major component at 100° C.) 4.02 (2H, s), 4.68 (2H, s), 4.88 (2H, br s), 6.90 (2H, m), 7.37 (7H, m), 7.60 (4H, m), 10.55 (1H, br s); NMR Spectrum (DMSO-$d_6$ of minor component at 100° C.) 4.05 (2H, s), 4.61 (2H, s), 4.88 (2H, br s), 6.89 (2H, m), 7.37 (7H, m), 7.60 (4H, m), 10.68 (1H, br s); Mass Spectrum m/Z 434 (M+H)$^+$; Elemental Analysis: calculated for $C_{24}H_{23}N_3O_5$. 1.0 $CF_3CO_2H$. 1.0 $H_2O$: C, 55.2%; H, 4.63%; N, 7.43%; found: C, 55.1%; H, 4.4%; N, 7.1%.

The necessary starting material was prepared as follows:

(a) A mixture of benzyl 4-hydroxybenzoate (4 g), t-butyl bromoacetate (3.7 g), powdered anhydrous potassium carbonate (2.4 g) and acetone (100 ml) was heated to reflux for 3 days. The reaction mixture was cooled and filtered and the filtrate was evaporated to dryness to give a viscous oil (6.37 g). A portion of this oil (3.4 g) was dissolved in methanol (30 ml) and ammonium formate (4 g) was added. The resultant solution was covered with a blanket of argon before a slurry of 10% Pd on C (100 mg) in methanol (5 ml), also under argon, was added. The reaction mixture was stirred at ambient temperature for 18 hours then the catalyst was filtered off through a pad of kieselguhr and washed with ethanol and water. The combined filtrate and washings were evaporated to dryness and the residue was partitioned between dichloromethane and aqueous sodium bicarbonate. The aqueous layer was separated, washed with dichloromethane and then carefully acidified with dilute aqueous citric acid solution. The solid precipitate was collected, washed with water and air-dried to give 4-t-butoxycarbonylmethoxybenzoic acid (1.45 g), as a white crystalline solid; m.p. 119–121° C.

(b) To a solution of the product of step (a) (100 mg), HBTU (152 mg) and HOBT (62 mg) in DMF (1.5 ml) under argon was added diisopropylethylamine (0.5 ml). After 2–3 minutes, solid N-benzylhydrazine dihydrochloride (156 mg) was added. The pale yellow reaction mixture was stirred at ambient temperature under argon overnight and then diluted with ethyl acetate (20 ml) and washed with water, dilute $KHSO_4$ (aq.), dilute NaOH (aq.), and with water, dried ($MgSO_4$) and evaporated to leave a mixture of t-butyl 4-(3-benzylcarbazoyl)phenoxyacetate and t-butyl 4-(2-benzylcarbazoyl)-phenoxyacetate as an oily residue (110 mg) which was not purified further. To this residue was added, under argon after 2–3 minutes, a pale yellow solution containing 4-t-butoxycarbonylaminomethylbenzoic acid (200 mg), HBTU (300 mg), HOBT (125 mg) and diisopropylethylamine (0.41 ml) in DMF (2 ml). The reaction mixture was stirred at ambient temperature under argon overnight and then diluted with ethyl acetate (20 ml) and washed with water, dilute $KHSO_4$ (aq.), dilute NaOH (aq.), and with water, dried ($MgSO_4$) and evaporated to leave an oily residue which was purified by column chromatography on silica, eluting with ethyl acetate/hexane, 1:2, to give a mixture of t-butyl 4-[2-benzyl-3-(4-t-butoxycarbonylaminomethylbenzoyl)carbazoyl]-phenoxyacetate and t-butyl 4-[3-benzyl-3-(4-t-butoxycarbonylaminomethylbenzoyl)carbazoyl] phenoxyacetate (150 mg) as an oil; NMR Spectrum (DMSO-$d_6$ at 100° C.) 1.30–1.45 (18H, brs), 4.10 (2H, m), 4.56 & 4.60 (2H, s & s), 4.82 (2H, br s), 6.85 (3H, m), 7.15–7.45 (7H, m), 7.49 (2H, d), 7.55 (2H, d), 10.46 & 10.53 (1H, s & s); Mass Spectrum m/Z 589 (M+H)$^+$.

EXAMPLE 12

Methyl 4-[3-(4-amidinobenzoyl)carbazoyl] phenoxyacetate, Acetate Salt

Methyl 4-[3-(4-thiocarbamoylbenzoyl)carbazoyl] phenoxyacetate (10.5 g) was suspended in acetone (1 L) and iodomethane (100 ml) was added. The reaction mixture was heated to 40–45° C. with stirring for 4 hours and then cooled to ambient temperature before a further aliquot of iodomethane (20 ml) was added. The reaction mixture was stirred at ambient temperature overnight. A further aliquot of iodomethane (20 ml) was added and the reaction mixture was heated again to 40–45° C. with stirring for 3 hours. Removal of the solvents in vacuo yielded methyl 4-[3-[4-(methylthio)carbonimidoylbenzoyl]carbazoyl] phenoxyacetate as an orange-brown solid which was not purified further. A portion of the residue (10 g) was suspended in a mixture of methanol (300 ml) and dichloromethane (300 ml), and covered with a blanket of argon before a solution of dry ammonium acetate (27 g) in methanol (100 ml) was added. The reaction mixture was stirred under argon for 2–3 days. Removal of the solvents in vacuo yielded a solid residue which was crystallised, with filtration, from boiling methanol to give the title compound (8.57 g) as a pale yellow solid; m.p. 208–210° C. (decomposes); NMR Spectrum (DMSO-$d_6$) 1.76 (3H, s), 3.72 (3H, s), 4.91 (2H, s), 7.06 (2H, d), 8.05 (2H, d), 7.90 (4H, m); Mass Spectrum m/Z 371 (M+H)$^+$; Elemental Analysis: calculated for $C_{18}H_{18}N_4O_5$. 1.0 $CH_3CO_2H$. 1.0 $CH_3OH$. 1.0 $H_2O$: C, 52.5%; H, 5.87%; N, 11.7%; found: C, 52.1%; H, 6.0%; N, 11.7%.

The necessary starting material was prepared as follows:

(a) In a similar manner to Example 9, starting material step (a), 4-methoxycarbonylmethoxybenzoic acid (580 mg), HBTU (1.04 g), HOBT (420 mg), diisopropylethylamine (1.41 ml), DMF (7.5 ml) and benzyl carbazate (500 mg) were reacted to give benzyl 3-(4-t-butoxycarbonylmethoxybenzoyl)carbazate (550 mg) as an off-white solid; NHR Spectrum (DMSO-$d_6$) 3.70 (3H, s), 4.88 (2H, s), 5.11 (2H, s), 7.03 (2H, d), 7.82 (2H, d), 7.38 (5H, m), 9.28 (1H, br s), 10.20 (1H, br s); Mass Spectrum m/z 359 (M+H)$^+$.

(b) To a solution of the product of step (a) (1 g) and 4-toluene-sulphonic acid hydrate (530 mg) in methanol (50 ml) under argon was added 10% Pd on C (200 mg). The mixture was covered with a blanket of hydrogen and stirred at ambient temperature for 3.5 hours. The catalyst was filtered off through a pad of kieselguhr and washed with methanol (50 ml). The combined filtrate and washings were evaporated to dryness. The oily residue was dissolved in dichloromethane (20 ml) and to this solution was added solid 4-cyanobenzoyl chloride (470 mg). The mixture was cooled with stirring to 0–5° C. before a solution of triethylamine (0.78 ml) in dichloromethane (10 ml) was added dropwise. On completion of the addition, the reaction mixture was stirred at 0–5° C. for 0.5 hours and at ambient temperature for 1.5 hours. The reaction mixture was evaporated to dryness and the residue was partitioned between ethyl acetate (100 ml), methanol (30 ml) and brine (50 ml). The organic layer was separated and washed with brine, dried ($MgSO_4$) and evaporated. The crude product was crystallised from methanol/chloroform/hexane (1:1:3) to give methyl 4-[3-(4-cyanobenzoyl)carbazoyl] phenoxyacetate (570 mg) as an off-white crystalline solid; m.p. 220–222° C.; NMR Spectrum (DMSO-$d_6$) 3.72 (3H, s), 4.89 (2H, s), 7.05 (2H, d) 7.89 (2H, d), 8.01 (2H, d), 8.06 (2H, d), 10.45 (1H, br s), 10.70 (1H, br s); Mass Spectrum m/Z 354 (M+H)$^+$.

(c) A solution of the product of step (b) (10 g) in a mixture of pyridine (500 ml) and triethylamine (80 ml) was covered with a blanket of $H_2S$ gas and stirred at ambient temperature overnight. The dark green reaction mixture was evaporated to dryness and the residue was triturated with dry ether. The resultant solid was collected and washed thoroughly with ether to give methyl 4-[3-(4-thiocarbamoylbenzoyl) carbazoyl]phenoxyacetate (10.5 g) as a yellow solid; NMR Spectrum (DMSO-$d_6$) 3.72 (3H, s), 4.90 (2H, s), 7.06 (2H, d), 7.90 (2H, d), 7.95 (4H, m), 9.62 (1H, br s), 10.01 (1H, br s), 10.40 (1H, br s), 10.55 (1H, br s); Mass Spectrum m/Z 388 (M+H)$^+$.

EXAMPLE 13

4-[3-(4-Amidinobenzoyl)carbazoyl]phenoxyacetic Acid

A filtered solution of the product of Example 12 (600 mg) in a mixture of glacial acetic acid (4 ml) and water (16 ml) was heated to 95–100 ° C. with stirring for 30–36 hours and then allowed to cool slowly to ambient temperature. The precipitated product was collected, washed with water and suspended in boiling methanol (30 ml). The solids which did not dissolve were collected, washed with methanol and ether and dried under vacuum to give the title compound (320 mg) as an off-white solid; NMR Spectrum (DMSO-$d_6$+ $CF_3CO_2H$) 4.83 (2H, s), 7.10 (2H, m), 7.98 (4H, m), 8.17 (2H, m), 8.23 (2H, br s), 8.38 (2H, br s); Mass Spectrum m/Z 357 (M+H)$^+$; Elemental Analysis: calculated for $C_{17}H_{16}N_4O_5$: C, 57.3%; H, 4.53%; N, 15.7%; found: C, 57.3%; H, 4.5%; N, 15.3%.

EXAMPLE 14

Methyl 4-[3-methyl-3-(4-amidinobenzoyl) carbazoyl]phenoxyacetate, Hydroiodide Salt In a similar manner to Example 12, methyl 4-[3-methyl-3-(4-thiocarbamoylbenzoyl)carbazoyl]phenoxyacetate (2 g) was reacted with iodomethane (15 ml) in acetone (200 ml) and the resultant product was treated with ammonium acetate (5 g), methanol (150 ml) and dichloromethane (150 ml). This yielded a crude yellow solid, which was triturated with methanol/dichloromethane, rather than crystallised, to give the title compound (800 mg) as a pale yellow hydroiodide salt; m.p. 208° C. (decomposes); NMR Spectrum (DMSO-$d_6$) 3.15–3.30 (3H, br), 3.70 (3H, s), 4.86 (2H, s), 6.97 (2H, d), 7.63 (2H, d), 7.67–7.80 (4H, m), 8.70–9.20 (4H, br s); Mass Spectrum m/Z 385 (M+H)$^+$; Elemental Analysis: calculated for $C_{19}H_{20}N_4O_5$. 1.0 HI. 1.0 $H_2O$: C, 43.0%; H, 4.4%; N, 10.6%; found: C, 43.4%; H, 4.5%; N, 10.1%.

The necessary starting material was prepared as follows:

(a) To a stirred suspension of 4-methoxycarbonylmethoxybenzoic acid (7.5 g) in dichloromethane (250 ml) containing DMF (1 drop) was added thionyl chloride (30 ml) and the resultant solution was heated to reflux for 5 hours. The solvents were removed in vacuo and the solid residue, containing crude 4-methoxycarbonylmethoxybenzoyl chloride, was used without further purification. A portion of the solid residue containing 4-methoxycarbonylmethoxybenzoyl chloride (3.5 g) was dissolved in dichloromethane (50 ml) and this solution was added dropwise with stirring over 40 minutes to an ice-cold solution of t-butyl 2-methylcarbazate (J. Chem. Soc. Perkin Trans. I (1975), 1712) (2 g) and triethylamine (3 ml) in dichloromethane (50 ml). The resultant solution was stirred at low temperature for 10 minutes and then at ambient temperature for 2 hours. A further quantity of dichloromethane (100 ml) was added and the solution was washed with water, dilute aqueous sodium bicarbonate solution and brine, dried ($MgSO_4$) and evaporated. The solid residue was crystallised from ethyl acetate/hexane to give methyl 4-(3-methy-3 -t-butoxycarbonylcarbazoyl)- phenoxyacetate (3.9 g) as a white solid; m.p. 158–159° C.; NMR Spectrum (DMSO-$d_6$ at 100° C.) 1.40 (9H, s), 3.10 (3H, s), 3.70 (3H, s), 4.80 (2H, s), 6.96–7.5 (2H, m), 7.73–7.80 (2H, m), 10.05 (1H, s); Mass Spectrum m/Z 339 (M+H)$^+$; Elemental Analysis: calculated for $C_{16}H_{22}N_2O_6$: C, 56.8%; H, 6.55%; N, 8.3%; found: C, 56.6%; H, 6.8%; N, 8.1%.

(b) To a stirred suspension of the product of step (a) (2.9 g) in a mixture of dichloromethane (20 ml) and anisole (2 ml) at 0–5° C. was added trifluoroacetic acid (27 ml). The resultant solution was stirred at low temperature for 20 minutes and then at ambient temperature for 2.5 hours. The reaction mixture was evaporated and the residue was triturated with dry ether. The solid was collected and washed with ether to give methyl 4-(3-methylcarbazoyl)-phenoxyacetate trifluoroacetate salt (2.9 g), as a white solid; m.p. 121–123° C.; NMR Spectrum (DMSO-$d_6$) 2.80 (3H, s), 3.70 (3H, s), 4.93 (2H, s), 7.10 (2H, d), 7.85 (2H, d), 10.80–11.70 (1H, br s); Mass Spectrum m/Z 239 (M+H)$^+$.

(c) In a similar manner to Example 12, the second portion of starting material step (b), the product of step (b) (2.9 g), 4-cyanobenzoyl chloride (1.55 g), dichloromethane (70 ml) and triethylamine (3.7 ml) were reacted to give, after crystallisation of the crude product from ethyl acetate/hexane, methyl 4-[3-methyl-3-(4-cyanobenzoyl)carbazoyl]-phenoxyacetate (2 g) as a white solid; m.p. 172–175° C.; NMR Spectrum (DMSO-$d_6$) 3.22 (3H, s), 3.69 (3H, s), 4.85 (2H, s), 6.97 (2H, d), 7.54–7.65 (4H, m), 7.82 (2H, m), 10.95 (1H, s); Mass Spectrum m/Z 368 (M+H)$^+$.

(d) In a similar manner to Example 12, starting material step (c), the product of step (c) (2 g), pyridine (182 ml), triethylamine (26 ml) and $H_2S$ gas were reacted to give methyl 4-[3-methyl-3-(4-thiocarbamoylbenzoyl)carbazoyl] phenoxyacetate (2.1 g) as a yellow solid; m.p. 169–170° C. (decomposes); NMR Spectrum (DMSO-$d_6$) 3.21 (3H, s), 3.68 (3H, s), 4.83 (2H, s), 6.95 (2H, d), 7.50–7.65 (4H, m), 7.83 (2H, d), 9.45–9.60 (1H, br), 9.80–9.90 (1H, br), 10.93 (1H, s).

EXAMPLE 15

4-[3-Methyl-3-(4-amidinobenzoyl)carbazoyl] phenoxyacetic Acid, Hydroiodide Salt

A solution of the product of Example 14 (98 mg) in a mixture of glacial acetic acid (0.7 ml) and water (2.5 ml) was heated to 90–95° C. for 24 hours. The reaction mixture was cooled to ambient temperature and washed with ether. The aqueous layer was separated, filtered and lyophilised overnight to give the title compound (80 mg) as a pale yellow solid; NMR Spectrum (DMSO-$d_6$) 1.92 (0.65H, s), 3.25 (3H, s), 4.70 (2H, s), 6.95 (2H, d), 7.62 (2H, d), 7.67–7.80 (4H, m), 8.9–9.4 (4H, br s), 10.95 (1H, s); Mass Spectrum m/Z 371 (M+H)$^+$; Elemental Analysis: calculated for $C_{18}H_{18}N_4O_5 \cdot 1.0$ HI. 0.2 $CH_3CO_2H$. 1.5 $H_2O$: C, 41.1%; H, 4.3%; N, 10.4%; found: C, 41.3%; H, 4.1%; N, 10.2%.

EXAMPLE 16

Methyl 4-[2-methyl-3-(4-amidinobenzoyl)carbazoyl] phenoxyacetate, Acetate Salt

In a similar manner to Example 12, methyl 4-[2-methyl-3-(4-thiocarbamoylbenzoyl)carbazoyl]phenoxyacetate (2.5 g) was reacted with iodomethane (15 ml) in acetone (150 ml) and the resultant product was treated with ammonium acetate (6.5 g), methanol (100 ml) and dichloromethane (100 ml). This yielded a crude yellow solid, which was triturated with methanol, collected and washed with methanol/dichloromethane, rather than crystallised, to give the title compound (1.3 g) as an off-white solid; m.p. 210° C. (decomposes); NMR Spectrum (DMSO-$d_6$) 1.73 (3H, s), 3.20 (3H, s), 3.55 (3H, s), 4.76 (2H, s), 6.90 (2H, d), 7.53 (2H, d), 7.80 (4H, m), 8.50–11.0 (2H, br s); Mass Spectrum m/Z 385 (M+H)$^+$; Elemental Analysis: calculated for $C_{19}H_{20}N_4O_5 \cdot 1.0$ $CH_3CO_2H$. 0.8 $H_2O$: C, 55.0%; H, 5.6%; N, 12.2%; found: C, 55.0%; H, 5.4%; N, 11.8%.

The necessary starting material was prepared as follows:

(a) A solution of 4-cyanobenzoyl chloride (2.5 g) in dichloromethane (50 ml) was added dropwise with stirring over 45 minutes to an ice-cold solution of t-butyl 2-methylcarbazate (2.0 g) in dichloromethane (50 ml) containing triethylamine (1.9 ml). The reaction mixture was stirred at ambient temperature for 2 hours and then washed with water, dilute aqueous sodium bicarbonate solution and brine, dried ($MgSO_4$) and evaporated. The residue was crystallised from ethyl acetate to give t-butyl 3-(4-cyanobenzoyl)-2-methylcarbazate (2.5 g) as a white solid; m.p. 179–181° C.; NMR Spectrum (DMSO-$d_6$) 1.27–1.55 (9H, br s), 3.10 (3H, br s), 8.00 (4H, s), 10.90 (1H, s); Mass Spectrum m/Z 276 (M+H)$^+$; Elemental Analysis: calculated for $C_{14}H_{17}N_3O_3$: C, 61.1%; H, 6.2%; N, 15.3%; found: C, 61.6%; H, 6.2%; N, 15.5%.

(b) In a similar manner to Example 14, starting material step (b), the product of step (a) (2.2 g), anisole (2 ml), dichloromethane (20 ml) and TFA (27 ml) were reacted to give N-(4-cyanobenzoyl)-N'-methylhydrazine, trifluoroacetate salt (2.3 g), as a white solid: m.p. 131–134° C.; NMR Spectrum (DMSO-$d_6$) 2.76 (3H, s), 8.00 (4H, s).

(c) In a similar manner to Example 14, the second portion of starting material step (a), crude 4-methoxycarbonylmethoxybenzoyl chloride (2 g), the product of step (b) (2.2 g), dichloromethane (50 ml total) and triethylamine (3.5 ml) was reacted to give, after crystallisation from ethyl acetate, methyl 4-[2-methyl-3-(4-cyanobenzoyl)carbazoyl]-phenoxyacetate (2.2 g) as a white solid; m.p. 158–159° C.; NMR Spectrum (DMSO-$d_6$) 3.21 (3H, s), 3.66 (3H, s), 4.79 (2H, s), 6.89 (2H, d), 7.48 (2H, d), 7.78 (2H, d), 7.93 (2H, d), 11.28 (1H, s); Mass Spectrum m/Z 368 (M+H)$^+$; Elemental Analysis: calculated for $C_{19}H_{17}N_3O_5$: C, 62.1%; H, 4.7%; N, 11.4%; found: C, 62.3%; H, 4.7%; N, 11.4%.

(d) In a similar manner to Example 12, starting material step (c), the product of step (c) (2.2 g), pyridine (182 ml), triethylamine (26 ml) and $H_2S$ gas were reacted to give methyl 4-[2-methyl-3-(4-thiocarbamoylbenzoyl)carbazoyl] phenoxyacetate (2.1 g) as a yellow solid; NMR Spectrum (DMSO-$d_6$) 3.20 (3H, s), 3.65 (3H, s), 4.78 (2H, s), 6.89 (2H, d), 7.51 (2H, d), 7.65 (2H, d), 7.86 (2H, d), 9.55–9.63 (1H, br s), 9.95–10.05 (1H, br s), 11.16 (1H, s).

EXAMPLE 17

4-[2-Methyl-3-(4-amidinobenzoyl)carbazoyl] phenoxyacetic Acid, Trifluoroacetate Salt In a similar manner to Example 15, the product of Example 16 (300 mg), glacial acetic acid (2 ml) and water (8 ml) were reacted to give a lyophilised material which was purified by reversed-phase column chromatography, using an acetonitrile/water mobile phase system containing 0.1% trifluoroacetic acid, to give the title compound (140 mg) as a white solid; NMR Spectrum (DMSO-$d_6$) 3.19 (3H, br s), 4.53 (2H, s), 6.75 (2H, d), 7.40 (2H, d), 7.67–7.80 (4H, m), 9.20 (2H, bs), 9.25 (2H, br s), 11.21 (1H, s); Mass Spectrum m/Z 371 (M+H)$^+$; Elemental Analysis: calculated for $C_{18}H_{18}N_4O_5 \cdot 1.0$ $CF_3CO_2H$. 0.25 $H_2O$: C, 49.1%; H, 4.0%; N, 11.5%; found: C, 48.9%; H, 4.0%; N, 11.5%.

EXAMPLE 18

Methyl 4-[3-(4-phenylamidinobenzoyl)carbazoyl] phenoxyacetate, Hydroiodide Salt

To a solution of methyl 4-[3-[4-(methylthio) carbonimidoylbenzoyl]carbazoyl]phenoxyacetate prepared as described in Example 12 (4.98 g) in methanol (60 ml) was added aniline (3.5 ml). The reaction mixture was heated to 50° C. and stirred at that temperature for 7 hours. The solvents were removed in vacuo and the residue was triturated with ether to give the title compound (5.52 g) as a cream solid; NMR Spectrum (DMSO-$d_6$) 3.72 (3H, s), 4.92 (2H, s), 6.55 (1H, m), 7.04 (3H, m), 7.55 (5H, m), 7.93 (2H, d), 8.05 (2H, d), 8.15 (2H, d); Mass Spectrum m/Z 447 (M+H)$^+$; Elemental Analysis: calculated for $C_{24}H_{22}N_4O_5$.1.0 HI: C, 50.1%; H, 4.0%; N, 9.7%; found: C, 50.1%; H, 4.1%; N, 9.5%.

EXAMPLE 19

4-[3-(4-Phenylamidinobenzoyl)carbazoyl]phenoxyacetic Acid, Sodium Salt

To a stirred suspension of the product of Example 18 (500 mg) in methanol (15 ml) was added 1.0 M NaOH (aq) solution (1.75 ml). The reaction mixture was stirred at ambient temperature overnight. An extra aliquot of 1.0 M NaOH (aq) solution (2 ml) was added and the reaction mixture was stirred at ambient temperature for a further 5 hours. The solvents were removed in vacuo and the residue was triturated with a small volume of water. The solids were collected by filtration and the procedure was repeated to give, in two combined crops, the title compound (234 mg) as a white solid; NMR Spectrum (DMSO-$d_6$) 4.21 (2H, s), 6.36 (2H, br s), 6.90 (4H, m), 6.99 (1H, m), 7.33 (2H, m), 7.85 (2H, d), 7.99 (2H, d), 8.09 (2H, d), 10.44 (2H, br s); Mass Spectrum m/Z 433 (M+Na)$^+$; Elemental Analysis: calculated for $C_{23}H_{20}N_4O_5$.1.0 Na.1.0 $H_2O$: C, 58.5%; H, 4.6%; N, 11.9%; found: C, 58.7%; H, 4.2%; N, 12.0%.

EXAMPLE 20

Illustrative pharmaceutical dosage forms suitable for presenting the compounds of the invention for therapeutic or prophylactic use include the following, which may be obtained by conventional procedures well known in the art.

|  | mg/tablet |
|---|---|
| a) Tablet I |  |
| Active ingredient | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |
| b) Tablet II |  |
| Active ingredient | 50 |
| Lactose | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| c) Tablet III |  |
| Active ingredient | 100 |
| Lactose | 182.75 |
| Croscarmellose sodium | 12.0 |
| Maize starch paste (5% w/v aqueous paste) | 2.25 |
| Magnesium stearate | 3.0 |
| (d) Capsule | mg/capsule |
| Active ingredient | 10 |
| Lactose Ph. Eur. | 488.5 |
| Magnesium stearate | 1.5 |

-continued

| (e) Injection | mg/ml |
|---|---|
| Active ingredient (acid addition salt) | 1.0 |
| Sodium chloride | 9.0 |
| Purified water to 1.0 ml |  |

CHEMICAL FORMULAE

I $R^1$—CON($R^2$)—N($R^3$)CO—$X^1$—Q—$X^2$—G

II

[Structure: aromatic ring with $Z^1$, substituents A and E]

III

[Structure: HN-piperidine-T—$X^3$—]

IV

[Structure: aromatic ring with $Z^2$, $Z^3$]

V

[Structure: N-piperidine with $Z^3$]

VI $R^1$—CON($R^2$)—N($R^3$)CO—$X^1$—Q—$X^2$—COO$G^1$

VII

[Structure: aromatic ring with $Z^1$, $A^1$, E, CON($R^2$)—N($R^3$)CO—$X^1$—Q—$X^2$—G]

VIII

[Structure: aromatic ring with $Z^1$, $A^1$, E, CON($R^2$)—N($R^3$)CO—$X^1$—Q—$X^2$—COO$G^1$]

IX $R^1$—COOH

X

HN($R^2$)—N($R^3$)CO—$X^1$—Q—$X^2$—G

XI $R^1$—CON($R^2$)—NH$R^3$

XII

HOOC—$X^1$—Q—$X^2$—G

XIII $R^1$—CON($R^2$)—N($R^3$)CO—$X^1$—Q—$X^{2a}$—G

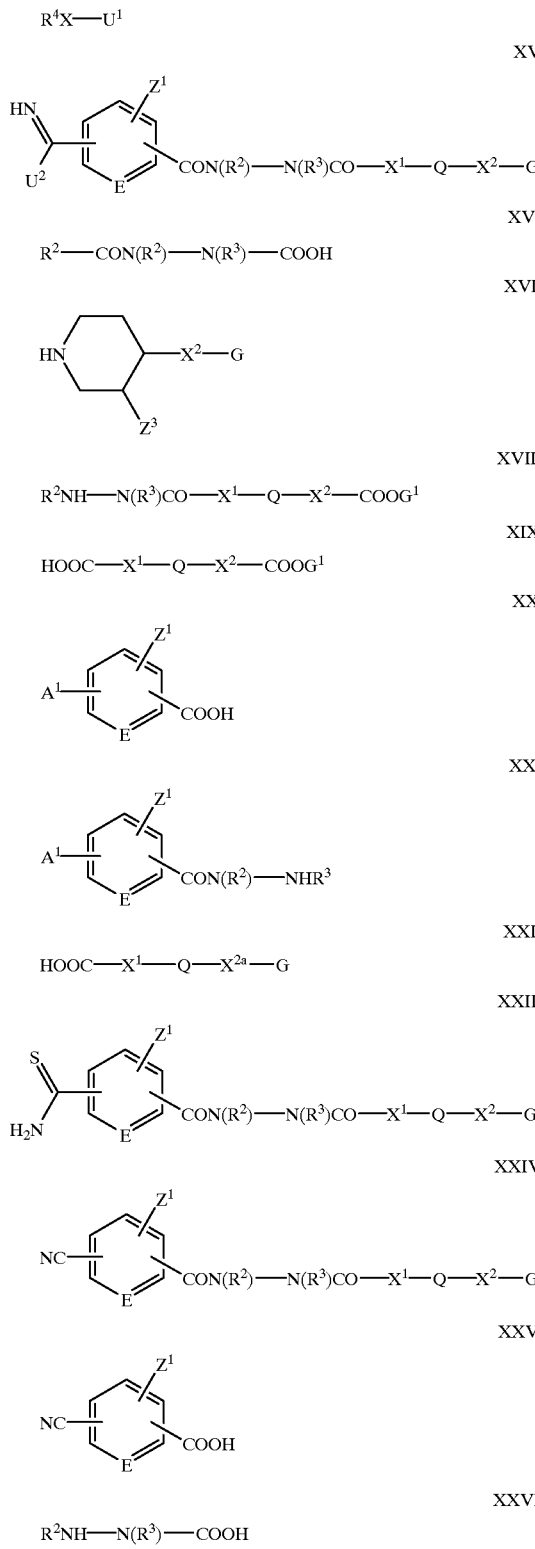

We claim:
1. An acid derivative of the formula (I)

R¹—CON(R²)—N(R³)CO—X¹—Q—X²—G    (I)

wherein R¹ represents a group of the formula (III)

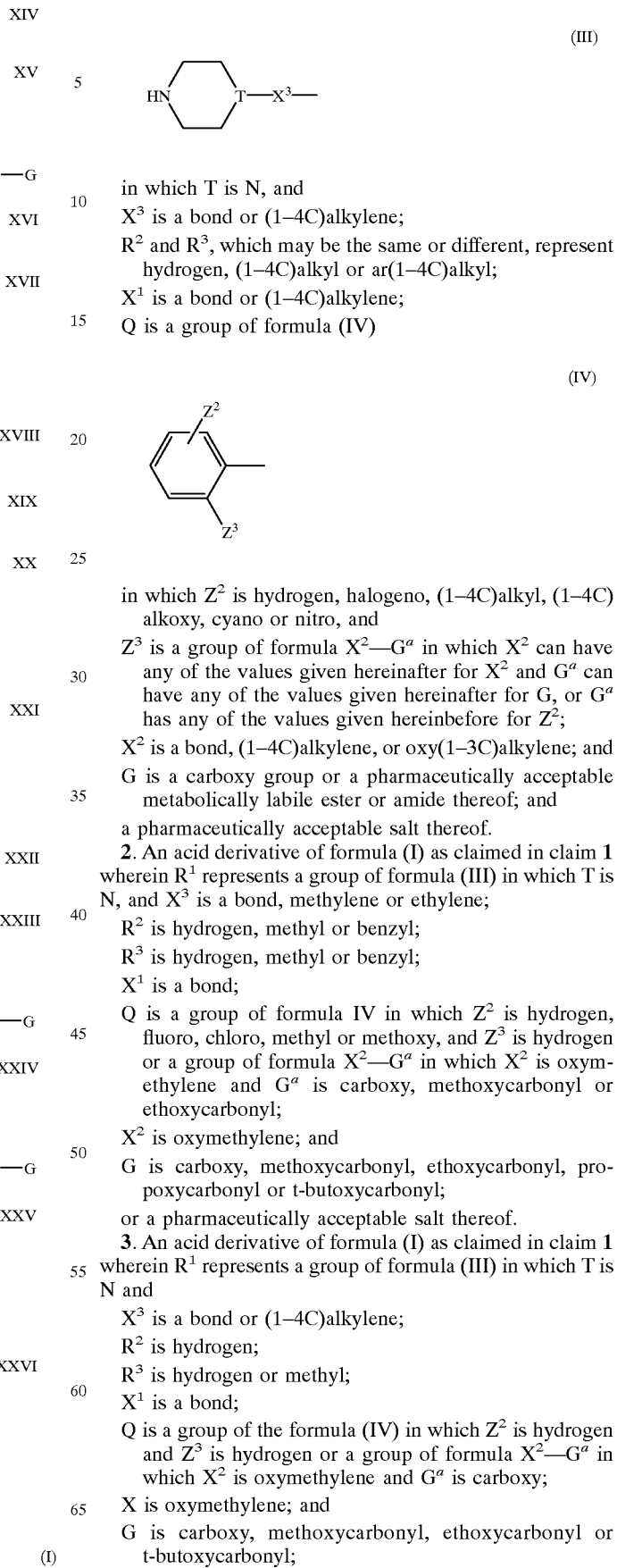

in which T is N, and
X³ is a bond or (1–4C)alkylene;
R² and R³, which may be the same or different, represent hydrogen, (1–4C)alkyl or ar(1–4C)alkyl;
X¹ is a bond or (1–4C)alkylene;
Q is a group of formula (IV)

in which Z² is hydrogen, halogeno, (1–4C)alkyl, (1–4C)alkoxy, cyano or nitro, and
Z³ is a group of formula X²—Gᵃ in which X² can have any of the values given hereinafter for X² and Gᵃ can have any of the values given hereinafter for G, or Gᵃ has any of the values given hereinbefore for Z²;
X² is a bond, (1–4C)alkylene, or oxy(1–3C)alkylene; and
G is a carboxy group or a pharmaceutically acceptable metabolically labile ester or amide thereof; and
a pharmaceutically acceptable salt thereof.

2. An acid derivative of formula (I) as claimed in claim 1 wherein R¹ represents a group of formula (III) in which T is N, and X³ is a bond, methylene or ethylene;
R² is hydrogen, methyl or benzyl;
R³ is hydrogen, methyl or benzyl;
X¹ is a bond;
Q is a group of formula IV in which Z² is hydrogen, fluoro, chloro, methyl or methoxy, and Z³ is hydrogen or a group of formula X²—Gᵃ in which X² is oxymethylene and Gᵃ is carboxy, methoxycarbonyl or ethoxycarbonyl;
X² is oxymethylene; and
G is carboxy, methoxycarbonyl, ethoxycarbonyl, propoxycarbonyl or t-butoxycarbonyl;
or a pharmaceutically acceptable salt thereof.

3. An acid derivative of formula (I) as claimed in claim 1 wherein R¹ represents a group of formula (III) in which T is N and
X³ is a bond or (1–4C)alkylene;
R² is hydrogen;
R³ is hydrogen or methyl;
X¹ is a bond;
Q is a group of the formula (IV) in which Z² is hydrogen and Z³ is hydrogen or a group of formula X²—Gᵃ in which X² is oxymethylene and Gᵃ is carboxy;
X is oxymethylene; and
G is carboxy, methoxycarbonyl, ethoxycarbonyl or t-butoxycarbonyl;

or a pharmaceutically acceptable salt thereof.

4. An acid derivative of formula (I) as claimed in claim 1 wherein $R^1$ represents a group of formula (III) in which T is N and $X^3$ is a bond;

$R^2$ is hydrogen;

$R^3$ is hydrogen or methyl;

$X^1$ is a bond;

Q is a group of formula IV in which $Z^2$ is hydrogen and $Z^3$ is hydrogen or a group of formula $X^2$—$G^a$ in which $X^2$ is oxymethylene $G^a$ is carboxy;

$X^2$ is oxymethylene; and

G is carboxy, methoxycarbonyl, ethoxycarbonyl or t-butoxycarbonyl;

a pharmaceutically acceptable salt thereof.

5. The compound 4-[3'-(piperazin-1-ylcarbonyl)carbazolyl]2-carboxymethoxy)phenoxy acetic acid; or a pharmaceutically acceptable salt thereof.

6. A process for the preparation of an acid derivative of formula (I)

$$R^1\text{—CON}(R^2)\text{—N}(R^3)\text{CO—}X^1\text{—Q—}X^2\text{—G} \quad (I)$$

or a pharmaceutically acceptable metabolically labile ester or amide thereof, or a pharmaceutically acceptable salt thereof, as claimed in claim 1 which process comprises:

(A) for a compound of formula (I) in which G is carboxy, deprotecting a compound of formula (VI)

$$R^1\text{—CON}(R^2)\text{—N}(R^3)\text{CO—}X^1\text{—Q—}X^2\text{—COOG}^1 \quad (VI)$$

in which $G^1$ is a carboxy protecting group;

(B) reacting a compound of formula (IX)

$$R^1\text{—COOH} \quad (IX)$$

or a reactive derivative thereof, with a compound of formula (X)

$$HN(R^2)\text{—N}(R^3)\text{CO—}X^1\text{—Q—}X^2\text{—G} \quad (X)$$

(C) reacting a compound of formula (XI)

$$R^1\text{—CON}(R^2)\text{—NHR}^3 \quad (XI)$$

with a compound of formula (XII)

$$HOOC\text{—}X^1\text{—Q—}X^2\text{—G} \quad (XII)$$

or a reactive derivative thereof; or (D) for a compound of formula (I) in which $X^2$ is a group of formula $CH_2CH(NHXR^4)$, reacting a compound of formula (XIII)

$$R^1\text{—CON}(R^2)\text{—N}(R^3)\text{CO—}X^1\text{—Q—}X^{2a}\text{—G} \quad (XIII)$$

in which $X^{2a}$ is $CH_2CH(NH_2)$, or an acid addition salt thereof, with a compound of formula (XIV)

$$R^4X\text{—}U^1 \quad (XIV)$$

in which $U^1$ is a leaving atom or group;

whereafter, optionally a compound of formula I is converted into a pharmaceutically acceptable metabolically labile ester or amide thereof, or a pharmaceutically acceptable salt thereof.

7. A method of inhibiting platelet aggregation in a warm-blooded mammal requiring such treatment, which comprises administering an effective amount of an acid derivative of formula (I), or a pharmaceutically acceptable metabolically labile ester or amide thereof, or a pharmaceutically acceptable salt thereof, as claimed in any one of claims 1–5.

8. A pharmaceutical composition comprising a compound of formula (I), or a pharmaceutically acceptable metabolically acceptable salt thereof, as claimed in any one of claims 1–5 together with a pharmaceutically acceptable diluent or carrier.

* * * * *